(12) United States Patent
Appenrodt et al.

(10) Patent No.: US 9,345,875 B2
(45) Date of Patent: May 24, 2016

(54) METHOD AND APPARATUS FOR CANNULA FIXATION FOR AN ARRAY INSERTION TUBE SET

(75) Inventors: Peter Appenrodt, Bremen (DE); Paulus Cornelis van Venrooij, Hoensbroek (NL)

(73) Assignee: Medtronic, Inc., Minneapolis, MN (US)

( * ) Notice: Subject to any disclaimer, the term of this patent is extended or adjusted under 35 U.S.C. 154(b) by 1794 days.

(21) Appl. No.: 12/104,844

(22) Filed: Apr. 17, 2008

(65) Prior Publication Data

US 2009/0264899 A1    Oct. 22, 2009

(51) Int. Cl.
| | | |
|---|---|---|
| *A61B 19/00* | (2006.01) | |
| *A61N 1/05* | (2006.01) | |
| *A61B 17/00* | (2006.01) | |
| *A61B 17/34* | (2006.01) | |

(52) U.S. Cl.
CPC ............ *A61N 1/0529* (2013.01); *A61B 19/201* (2013.01); *A61B 19/203* (2013.01); *A61B 19/5244* (2013.01); *A61B 2017/00477* (2013.01); *A61B 2017/3407* (2013.01); *A61B 2017/3409* (2013.01); *A61B 2019/304* (2013.01); *A61B 2019/5251* (2013.01); *A61B 2019/5255* (2013.01); *A61N 1/0534* (2013.01); *A61N 1/0539* (2013.01)

(58) Field of Classification Search
CPC ..................... A61B 19/201; A61B 2017/3407; A61B 2017/3409; A61B 2019/304; A61B 17/3403; A61B 2017/1728; A61B 2017/3405; A61B 2017/3411; A61B 19/22; A61B 19/30; A61B 2019/207; A61B 2019/208; A61B 2019/303; A61N 1/0539; A61M 25/02; A61M 2025/024; A61M 2025/028
USPC .................. 604/118; 606/71, 87–88, 105, 282
See application file for complete search history.

(56) References Cited

U.S. PATENT DOCUMENTS

| | | | |
|---|---|---|---|
| 5,592,939 A | 1/1997 | Martinelli | |
| 5,649,936 A | 7/1997 | Real | |
| 5,788,713 A | 8/1998 | Dubach et al. | |

(Continued)

FOREIGN PATENT DOCUMENTS

| | | | |
|---|---|---|---|
| WO | WO-9513758 | 5/1995 | |
| WO | WO-03039386 | 5/2003 | |
| WO | WO 03039386 A1 * | 5/2003 | ............. A61B 19/00 |

OTHER PUBLICATIONS

International Search Report and Written Opinion for PCT/US2009/030825 mailed May 8, 2009, claiming benefit of U.S. Appl. No. 12/104,844, filed Apr. 17, 2008.

(Continued)

*Primary Examiner* — David C Eastwood
*Assistant Examiner* — Martin T Ton
(74) *Attorney, Agent, or Firm* — Harness, Dickey & Pierce, P.L.C.

(57) ABSTRACT

An instrument holding system for a drive system is provided. The system can include an array holder that defines at least one bore for receipt of an instrument therethrough. The at least one instrument can be adapted for insertion into an anatomy. The array holder can be in communication with the drive system to receive a driving force. The system can include a fixation plate operable to move relative to the array holder such that the fixation plate is in contact with at least a portion of the at least one instrument to couple the at least one instrument to the array holder to enable the at least one instrument to be driven by the driving force into the anatomy.

16 Claims, 15 Drawing Sheets

(56) References Cited

U.S. PATENT DOCUMENTS

| | | | |
|---|---|---|---|
| 5,871,487 A | 2/1999 | Warner et al. | |
| 5,913,820 A | 6/1999 | Bladen et al. | |
| 5,928,143 A | 7/1999 | McNaughton | |
| 6,381,485 B1 | 4/2002 | Hunter et al. | |
| 6,474,341 B1 | 11/2002 | Hunter et al. | |
| 6,482,182 B1 | 11/2002 | Carroll et al. | |
| 6,493,573 B1 | 12/2002 | Martinelli et al. | |
| 6,516,212 B1 | 2/2003 | Bladen et al. | |
| 7,033,326 B1* | 4/2006 | Pianca et al. | 600/585 |
| 7,177,701 B1 | 2/2007 | Pianca | |
| 2002/0052610 A1 | 5/2002 | Skakoon et al. | |
| 2003/0114752 A1 | 6/2003 | Henderson et al. | |
| 2004/0215071 A1 | 10/2004 | Frank et al. | |
| 2005/0021118 A1* | 1/2005 | Genau et al. | 607/116 |
| 2005/0049486 A1 | 3/2005 | Urquhart et al. | |
| 2005/0085714 A1 | 4/2005 | Foley et al. | |
| 2005/0085720 A1 | 4/2005 | Jascob et al. | |
| 2006/0190055 A1* | 8/2006 | Malinowski et al. | 607/45 |
| 2007/0250077 A1* | 10/2007 | Skakoon et al. | 606/130 |
| 2008/0255544 A1 | 10/2008 | Gielen et al. | |
| 2008/0269777 A1 | 10/2008 | Appenrodt et al. | |

OTHER PUBLICATIONS

Mer MikroSonden Vorschub, "MicroDriven", http://www.inomed.com/english/content/produktgruppen/mer/mer-mikroson.htm printed Oct. 24, 2008.

microTargeting™ Neural Devices, FHC, Inc., (pp. 1-4, L022/Cat. p. 55-58. Rev. 071126).

Pollak, M.D., et al., Intraoperative Micro- and Macrostimulation of the Subthalamic Nucleus in Parkinson's Disease, Movement Disorders vol. 17, Suppl. 3, 2002, pp. S155-S161 (2002).

\* cited by examiner

METHOD AND APPARATUS FOR CANNULA FIXATION FOR AN ARRAY INSERTION TUBE SET

FIELD

The present disclosure relates generally to a neurosurgical procedure, and more specifically, to methods and apparatuses for cannula fixation for an array insertion tube set.

BACKGROUND

The statements in this section merely provide background information related to the present disclosure and may not constitute prior art.

A surgical procedure can be performed on various portions of an anatomy, such as a human anatomy. The surgical procedures can be invasive to varying degrees, such as by performing an open procedure or by performing a less invasive procedure. A procedure can be performed in a less invasive manner by minimizing or attempting to minimize an incision or portal formed in the tissue of the anatomy, opening through bone, and other minimization techniques.

A less invasive procedure, however, can also reduce visualization of a portion of the anatomy upon which a procedure is occurring, reduce access with various instruments to a portion of the anatomy, and the like. The less invasive procedure may also require specialized and particular instruments to perform the procedure in an appropriate and beneficial manner. It is desirable, therefore, to provide instruments, procedures, and the like to achieve an optimal outcome while maintaining the less invasive procedure.

Instruments, according to various applications, can be guided with exterior guide tools or systems to a selected portion of the anatomy to perform the procedure in the less invasive manner. For example, a scope can be guided along a selected portion of the anatomy for viewing an internal structure within the anatomy. Various other instruments can also be guided into the anatomy for various procedures. For example, at least one electrode can be guided into a portion of the anatomy, such as the brain. Each of the at least one electrode can include a microelectrode (ME), probe, deep brain stimulator (DBS), macroelectrode or combinations thereof. The ME or macroelectrode can be used to record electrical activity within the brain, and the at least one probe, deep brain stimulator or macroelectrode can then be guided into the anatomy in an area of interest as indicated by the recording to deliver electrical therapy to the patient.

In order to guide the electrode into the anatomy, such as the brain, a drive system can be employed. The drive system can include a guide portion that receives the at least one electrode. The guide portion can be configured to clamp or otherwise secure the at least one electrode to the drive system, such that the drive system can advance the at least one electrode into the anatomy. When multiple electrodes are employed, the clamp of the drive system may not always apply an equal holding force to each of the electrodes, which may only result in the partial advancement of one or more of the electrodes. Accordingly, it would be desirable to provide methods and apparatuses for cannula fixation for an array insertion tube set to facilitate the insertion of at least one electrode into an anatomy during a neurosurgical procedure.

SUMMARY

An instrument holding system for a drive system is provided. The system can include an array holder that defines at least one bore for receipt of an instrument therethrough. The at least one instrument can be adapted for insertion into an anatomy. The array holder can be in communication with the drive system to receive a driving force. The system can include a fixation plate operable to move relative to the array holder such that the fixation plate is in contact with at least a portion of the at least one instrument to couple the at least one instrument to the array holder to enable the at least one instrument to be driven by the driving force into the anatomy.

Further provided is an instrument holding system for a drive system. The system can include a support coupled to the drive system that receives a driving force from the drive system. The system can include a fixation block that defines at least one bore for receipt of at least one electrode therethrough. The fixation block can have a first side opposite a second side, with the first side and the second side each defining a mating feature. The system can also include a guide member coupled to the fixation block. The guide member can define at least one bore for receipt of the at least one electrode therethrough. The at least one bore of the guide member can be aligned with the at least one bore of the fixation block to enable the at least one electrode to pass through the fixation block and the guide member. The guide member can be coupled to the support to receive the driving force. The system can include a fixation plate having a first side and a second side that can each define a corresponding mating feature that can be operable to slideably engage the mating feature of the fixation block to enable the fixation plate to move relative to the fixation block between a first position and a second position. In the second position, the fixation plate can be in contact with at least a portion of a surface of the at least one electrode to couple the at least one electrode to the support such that on receipt of the driving force, a portion of the at least one electrode can move relative to an anatomy.

Also provided is a method of coupling an instrument to a drive system. The method can include coupling an array holder to the drive system. The method can also include inserting at least one electrode into at least one bore defined in the array holder. The method can include positioning a fixation plate relative to the array holder. The method can further include moving the fixation plate relative to the array holder from a first position to a second position such that the fixation plate is in contact with at least a portion of a depth stop of the at least one electrode.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
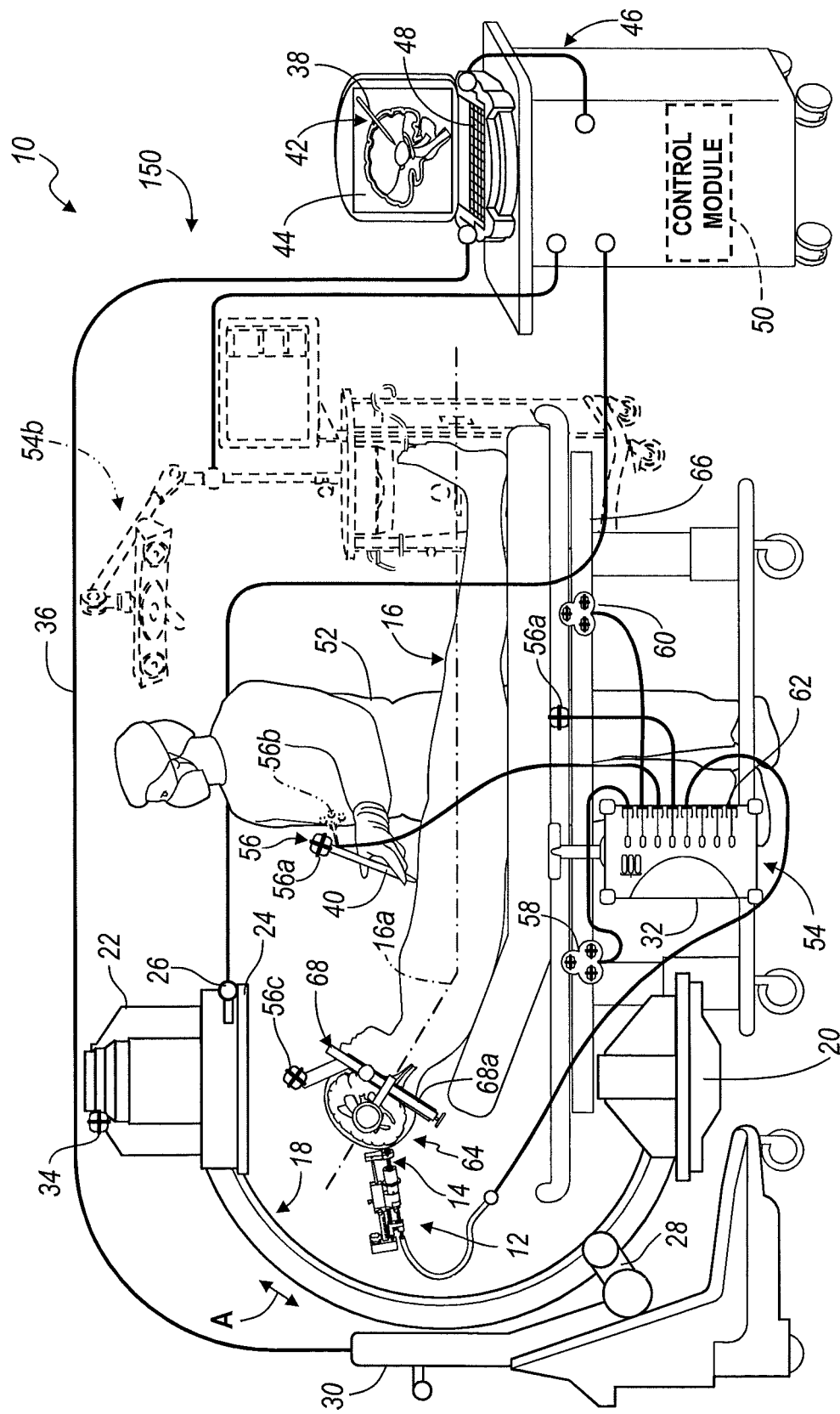
FIG. 1 is a diagram of a navigation system according to various embodiments of the present disclosure, which includes an exemplary drive system for inserting one or more instruments into an anatomy.

The following description is merely exemplary in nature and is not intended to limit the present disclosure, application, or uses. It should be understood that throughout the drawings, corresponding reference numerals indicate like or corresponding parts and features. As indicated above, the present teachings are directed toward providing a system and method for cannula fixation for an array insertion tube set during a surgical procedure. It should be noted, however, that the present teachings could be applicable to other appropriate procedures. Therefore, it will be understood that the following discussions are not intended to limit the scope of the appended claims.

As will be discussed in greater detail herein, the present disclosure is directed toward a system and method for cannula fixation for an array insertion tube set, which can be guided into an anatomy, such as a brain, by a drive system. In this regard, this system and method can include the use of a drive system 12 to control the insertion and withdrawal of one or more instruments 14 from the anatomy. The drive system 12 and the instruments 14 can be used in an operating theater, including an exemplary surgical navigation system 10, as illustrated in FIG. 1. Various surgical navigation systems can include those described in U.S. patent application Ser. No. 10/651,267 (now U.S. Pat. App. Pub No. 2005/0049486), filed on Aug. 28, 2003, incorporated herein by reference.

The exemplary surgical navigation system 10 can include an image based system, an imageless system, an atlas or diagram based system, or combinations thereof. One skilled in the art will understand that the surgical navigation system 10 can require the registration of a patient 16, which defines patient space, to a tracking system, discussed further herein. According to various embodiments, registration can include registration between image space, defined by image data or atlas data, and the patient space. It will be understood, however, that the surgical navigation system 10, as discussed with regard to FIG. 1, is merely optional, and any appropriate technique and/or system could be used to control the insertion and withdrawal of the electrodes 14, such as a robotic arm, stereotactic head frame, etc. Thus, it will be understood that the foregoing discussion of the exemplary navigation system 10 will not limit the appended claims to require a navigation system or a tracking system, as disclosed herein.

With continued reference to FIG. 1, the navigation system 10 that can be used for various procedures is illustrated. The navigation system 10 can be used to track the location of an implant, such as a spinal implant or orthopedic implant, or a surgical device, such as an electrode, relative to a patient 16. Also the navigation system 10 can track the position and orientation of various instruments 14. It should further be noted that the navigation system 10 may be used to navigate any type of instrument, implant, or delivery system, including: guide wires, arthroscopic systems, cardiac leads, orthopedic implants, spinal implants, deep-brain stimulator (DBS) probes, microelectrode recorder probes, macroelectrode stimulation probes, etc. Moreover, these instruments may be used to navigate or map any region of the body. The navigation system 10 and the various instruments may be used in any appropriate procedure, such as one that is generally minimally invasive, arthroscopic, percutaneous, stereotactic, or an open procedure.

Although an exemplary navigation system 10 that can include the imaging device 18 is discussed herein, one skilled in the art will understand that the disclosure is merely for clarity of the present discussion and any appropriate imaging system, navigation system, patient specific data, and non-patient specific data can be used. For example, the intraoperative imaging system can include an MRI imaging system, such as the PoleStar® MRI or an O-arm™ imaging system sold by Medtronic, Inc. It will be understood that the navigation system 10 can incorporate or be used with any appropriate preoperatively or intraoperatively acquired image data. For example, various imageless systems can be used or images from atlas models can be used to produce patient images, such as those disclosed in U.S. Patent Pub. No. 2005-0085714, filed Oct. 16, 2003, entitled "METHOD AND APPARATUS FOR SURGICAL NAVIGATION OF A MULTIPLE PIECE CONSTRUCT FOR IMPLANTATION," incorporated herein by reference. The imaging device 18 can be, for example, a fluoroscopic x-ray imaging device that may be configured as an O-arm™ or a C-arm, which can have an x-ray source 20, an x-ray receiving section 22, an optional calibration and tracking target 24 and optional radiation sensors 26.

In operation, the imaging device 18 can generate x-rays from the x-ray source 20 that can propagate through the patient 16 and calibration and/or tracking target 24, into the x-ray receiving section 22. This allows direct visualization of the patient 16 and radio-opaque instruments in the cone of the X-rays. In the example of FIG. 1, a longitudinal axis 16a of the patient 16 is substantially in line with a mechanical axis 28 of the C-arm. This can enable the imaging device 18 to be rotated relative to the patient 16, allowing images of the patient 16 to be taken from multiple directions or about multiple planes. An example of a fluoroscopic C-arm X-ray device that may be used as the optional imaging device 18 is the "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

When the x-ray source 20 generates the x-rays that propagate to the x-ray receiving section 22, the radiation sensors 26 can sense the presence of radiation, which is forwarded to an imaging device controller 30, to identify whether or not the imaging device 18 is actively imaging. This information can also be transmitted to a coil array controller 32, further discussed herein.

The imaging device controller 30 can capture the x-ray images received at the x-ray receiving section 22 and store the images for later use. Multiple two-dimensional images taken by the imaging device 18 may also be captured and assembled by the imaging device controller 30 to provide a larger view or image of a whole region of the patient 16, as opposed to being directed to only a portion of a region of the patient 16. The controller 30 may also be separate from the imaging device 18 and/or control the rotation of the imaging device 18. For example, a C-arm can move in the direction of arrow A or rotate about the longitudinal axis 16a of the patient 16, allowing anterior or lateral views of the patient 16 to be imaged. Each of these movements involves rotation about the mechanical axis 28 of the C-arm. The movements of the imaging device 18, such as the C-arm, can be tracked with a tracking device 34.

While the imaging device 18 is shown in FIG. 1 as a C-arm, any other alternative 2D, 3D or 4D imaging modality may also be used. For example, any 2D, 3D or 4D imaging device, such as the O-arm™ imaging device, isocentric fluoroscopy, bi-plane fluoroscopy, ultrasound, computed tomography (CT), multi-slice computed tomography (MSCT), magnetic resonance imaging (MRI), high frequency ultrasound (HFU), positron emission tomography (PET), optical coherence tomography (OCT), intra-vascular ultrasound (IVUS), ultrasound, intra-operative CT or MRI may also be used to acquire 2D, 3D or 4D pre- or post-operative and/or real-time images or patient image data 36 of the patient 16. For example, an intra-operative MRI system, may be used such as the PoleStar® MRI system sold by Medtronic, Inc.

In addition, image datasets from hybrid modalities, such as positron emission tomography (PET) combined with CT, or single photon emission computer tomography (SPECT) combined with CT, could also provide functional image data superimposed onto anatomical data to be used to confidently reach target sites within the patient 16. It should further be noted that the imaging device 18 as shown in FIG. 1, provides a virtual bi-plane image using a single-head C-arm fluoroscope as the imaging device 18 by simply rotating the C-arm about at least two planes, which could be orthogonal planes, to generate two-dimensional images that can be converted to three-dimensional volumetric images. By acquiring images in more than one plane, an icon 38 representing the location of the instrument 14, such as an impacter, stylet, reamer driver, taps, drill, deep-brain stimulator (DBS) probes, cardiac leads or other instrument, or implantable devices introduced and advanced in the patient 16, may be superimposed in more than one view and included in image data 42 displayed on a display 44, as will be discussed.

If the imaging device 18 is employed, patient image data 36 can be forwarded from the imaging device controller 30 to a navigation computer and/or processor or workstation 46. It will also be understood that the patient image data 36 is not necessarily first retained in the imaging device controller 30, but may also be directly transmitted to the workstation 46. The workstation 46 can include the display 44, a user input device 48 and a control module 50. The workstation 46 can also include or be connected to an image processor, navigation processor, and memory to hold instruction and data. The workstation 46 can provide facilities for displaying the patient image data 36 as an image on the display 44, saving, digitally manipulating, or printing a hard copy image of the received patient image data 36.

The user input device 48 can comprise any device that can enable a user to interface with the workstation 46, such as a touchpad, touch pen, touch screen, keyboard, mouse, wireless mouse, or a combination thereof. The user input device 48 allows a physician or user 52 to provide inputs to control the imaging device 18, via the imaging device controller 30, adjust the display settings of the display 44, or control a tracking system 54, as further discussed herein. The control module 50 can determine the location of a tracking device 56 with respect to the patient space, and can output image data 42 to the display 44.

With continuing reference to FIG. 1, the navigation system 10 can further include the electromagnetic navigation or tracking system 54. A representative electromagnetic navigation or tracking system 54 can include the AXIEM™ electromagnetic tracking system sold by Medtronic Navigation, Inc. The tracking system 54 can include a localizer, such as a first coil array 58 and/or second coil array 60, the coil array controller 32, a navigation probe interface 62, the device or instrument 14, a patient tracker or dynamic reference frame (DRF) 64, and one or more tracking devices 56. Other tracking systems can include an optical tracking system 54b, for example the StealthStation® Treon® and the StealthStation® Tria® both sold by Medtronic Navigation, Inc. Further, other tracking systems can be used that include acoustic, radiation, radar, infrared, etc., or hybrid systems, such as a system that includes components of both an electromagnetic and optical tracking system, etc. The drive system 12, the instrument 14 and the DRF 64 can each include tracking device(s) 56.

The tracking device 56 or any appropriate tracking device as discussed herein, can include both a sensor, a transmitter, or combinations thereof and can be indicated by the reference numeral 56. Further, the tracking device 56 can be wired or wireless to provide a signal or emitter or receive a signal from a system. For example, a tracking device 56a can include one or more electromagnetic coils, such as a tri-axial coil, to sense a field produced by the localizing coil array 58 or 60. One will understand that the tracking device(s) 56 can receive a signal, transmit a signal, or combinations thereof to provide information to the navigation system 10, which can be used to determine a location of the tracking device 56. The navigation system 10 can determine a position of the instrument 14 and the DRF 64 based on the location of the tracking device(s) 56 to allow for accurate navigation relative to the patient 16 in the patient space.

With regard to the optical localizer or tracking system 54b, the optical tracking system 54b can transmit and receive an optical signal, or combinations thereof. An optical tracking device 56b can be interconnected with the instrument 14, or other devices such as the DRF 64. As generally known, the optical tracking device 56b can reflect, transmit or receive an optical signal to/from the optical localizer or tracking system 54b that can be used in the navigation system 10 to navigate or track various elements. Therefore, one skilled in the art will understand, that the tracking device(s) 56 can be any appropriate tracking device to work with any one or multiple tracking systems.

The coil arrays 58, 60 can transmit signals that are received by the tracking device(s) 56. The tracking device(s) 56 can then transmit or receive signals based upon the transmitted or received signals from or to the coil arrays 58, 60. The coil arrays 58, 60 are shown attached to an operating table 66. It should be noted, however, that the coil arrays 58, 60 can also be positioned at any other location, as well and can also be positioned in the items being navigated. The coil arrays 58, 60 include a plurality of coils that are each operable to generate distinct electromagnetic fields into the navigation region of the patient 16, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil arrays 58, 60 can be controlled or driven by the coil array controller 32. The coil array controller 32 can drive each coil in the coil arrays 58, 60 in a time division multiplex or a frequency division multiplex manner. In this regard, each coil can be driven separately at a distinct time or all of the coils can be driven simultaneously with each being driven by a different frequency. Upon driving the coils in the coil arrays 58, 60 with the coil array controller 32, electromagnetic fields are generated within the patient 16 in the area where the medical procedure is being performed, which is again sometimes referred to as patient space. The electromagnetic fields generated in the patient space induce currents in a tracking device(s) 56 positioned on or in the drive system 12, the instrument 14 and the DRF 64. These induced signals from the drive system 12, the instrument 14 and the DRF 64 are delivered to the navigation probe interface 62 and can be subsequently forwarded to the coil array controller 32.

The navigation probe interface 62 may provide the necessary electrical isolation for the navigation system 10. The navigation probe interface 62 can also include amplifiers, filters and buffers to directly interface with the tracking device(s) 56 in the instrument 14 and DRF 64. Alternatively, the tracking device(s) 56, or any other appropriate portion, may employ a wireless communications channel, such as that disclosed in U.S. Pat. No. 6,474,341, entitled "Surgical Communication Power System," issued Nov. 5, 2002, incorporated herein by reference, as opposed to being coupled directly to the navigation probe interface 62.

The instrument 14 may be any appropriate instrument, such as an instrument for preparing a portion of the patient 16, an instrument for recording activity in a portion of the anatomy or an instrument for positioning an implant. The DRF 64, according to various embodiments, can include a small magnetic field detector. The DRF 64 may be fixed to the patient 16 adjacent to the region being navigated so that any movement of the patient 16 is detected as relative motion between the coil arrays 58, 60 and the DRF 64. This relative motion is forwarded to the coil array controller 32, which updates registration correlation and maintains accurate navigation, further discussed herein. The DRF 64 may include any appropriate tracking device 56 used by the navigation system 10. Therefore, the DRF 64 can include an optical tracking device, as indicated by reference number 56b, or acoustic, etc. For example, the DRF 64 can include a DRF holder or head frame 68 and a removable tracking device 56c. Alternatively, the DRF 64 can include a tracking device 56 that can be formed integrally or separately from the head frame 68.

Moreover, the DRF 64 can be provided as separate pieces and can be positioned at any appropriate position on the anatomy. For example, the tracking device 56c of the DRF 64 can be fixed to the skin of the patient 16 with an adhesive. Also, the DRF 64 can be positioned near a leg, arm, etc. of the patient 16. Thus, the DRF 64 does not need to be provided with the head frame 68 or require any specific base or holding portion. If the DRF 64 is used with an electromagnetic tracking device 56a, it can be configured as a pair of orthogonally oriented coils, each having the same center or may be configured in any other non-coaxial or co-axial coil configurations, such as a tri-axial coil configuration (not specifically shown).

Briefly, the navigation system 10 operates as follows. The navigation system 10 creates a translation map between all points in the radiological image generated from the imaging device 18 in image space and the corresponding points in the anatomical structure of the patient 16 in patient space. After this map is established, whenever a tracked instrument, such as the instrument 14 is used, the workstation 46 in combination with the coil array controller 32 and the imaging device controller 30 uses the translation map to identify the corresponding point on the pre-acquired image or atlas model, which is displayed on display 44. This identification is known as navigation or localization. The icon 38 representing the localized point or instruments 40 can be shown as image data 42 on the display 44.

To enable navigation, the navigation system 10 must be able to detect both the position of the anatomical structure of the patient 16 and the position of the instrument 14. Knowing the location of these two items allows the navigation system 10 to compute and display the position of the instrument 14 in relation to the patient 16 on the display 44. The tracking system 54 can be employed to track the instrument 14 and the anatomical structure simultaneously.

The tracking system 54, if using an electromagnetic tracking assembly, essentially works by positioning the coil arrays 58, 60 adjacent to the patient space to generate a low-energy electromagnetic field generally referred to as a navigation field. Because every point in the navigation field or patient space is associated with a unique field strength, the tracking system 54 can determine the position of the instrument 14 by measuring the field strength at the tracking device 56 location. The DRF 64 can be fixed to the patient 16 to identify a first location of the patient 16 in the navigation field. The tracking system 54 can continuously recompute the relative position of the DRF 64 and the instrument 14 during localization and relate this spatial information to patient registration data to enable image guidance of the instrument 40 within and/or relative to the patient 16.

Patient registration is the process of determining how to correlate the position of the drive system 12 and/or the instrument 14 relative to the patient 16 to the position on the diagnostic or pre-acquired images. To register the patient 16, a physician or user 52 may use point registration by selecting and storing particular points from the pre-acquired images and then touching the corresponding points on the anatomical structure of the patient 16 with a tracked pointer probe 40. The navigation system 10 analyzes the relationship between the two sets of points that are selected and computes a match, which correlates every point in the patient image data 36 with its corresponding point on the anatomical structure of the patient 16 or the patient space, as discussed herein. The points that are selected to perform registration are fiducial markers, such as anatomical landmarks. Again, the landmarks or fiducial markers are identifiable on the images and identifiable and accessible on the patient 16. The fiducial markers can be artificial markers that are positioned on the patient 16 or anatomical landmarks that can be easily identified in the patient image data 36. The artificial landmarks, such as the fiducial markers, can also form part of the DRF 64, such as those disclosed in U.S. Pat. No. 6,381,485, entitled "Registration of Human Anatomy Integrated for Electromagnetic Localization," issued Apr. 30, 2002, herein incorporated by reference.

The navigation system 10 may also perform registration using anatomic surface information or path information as is known in the art. The navigation system 10 may also perform 2D to 3D registration by utilizing the acquired 2D images to register 3D volume images by use of contour algorithms, point algorithms or density comparison algorithms, as is known in the art. An exemplary 2D to 3D registration procedure, is set forth in U.S. Ser. No. 10/644,680, entitled "Method and Apparatus for Performing 2D to 3D Registration" filed on Aug. 20, 2003, hereby incorporated by reference.

In order to maintain registration accuracy, the navigation system 10 continuously tracks the position of the patient 16 during registration and navigation. This is because the patient 16, DRF 64 and coil arrays 58, 60 may all move during the procedure, even when this movement is not desired. Therefore, if the navigation system 10 did not track the position of the patient 16 or area of the anatomy, any patient movement after image acquisition would result in inaccurate navigation within that image. Because the DRF 64 can be coupled to the patient 16, any movement of the anatomical structure of the patient 16 or the coil arrays 58, 60 can be detected as the relative motion between the coil arrays 58, 60 and the DRF 64. Both the relative motion of the coil arrays 58, 60 and the DRF 64 can be communicated to the coil array controller 32, via the navigation probe interface 62, which can update the registration correlation to thereby maintain accurate navigation.

Figure 2:
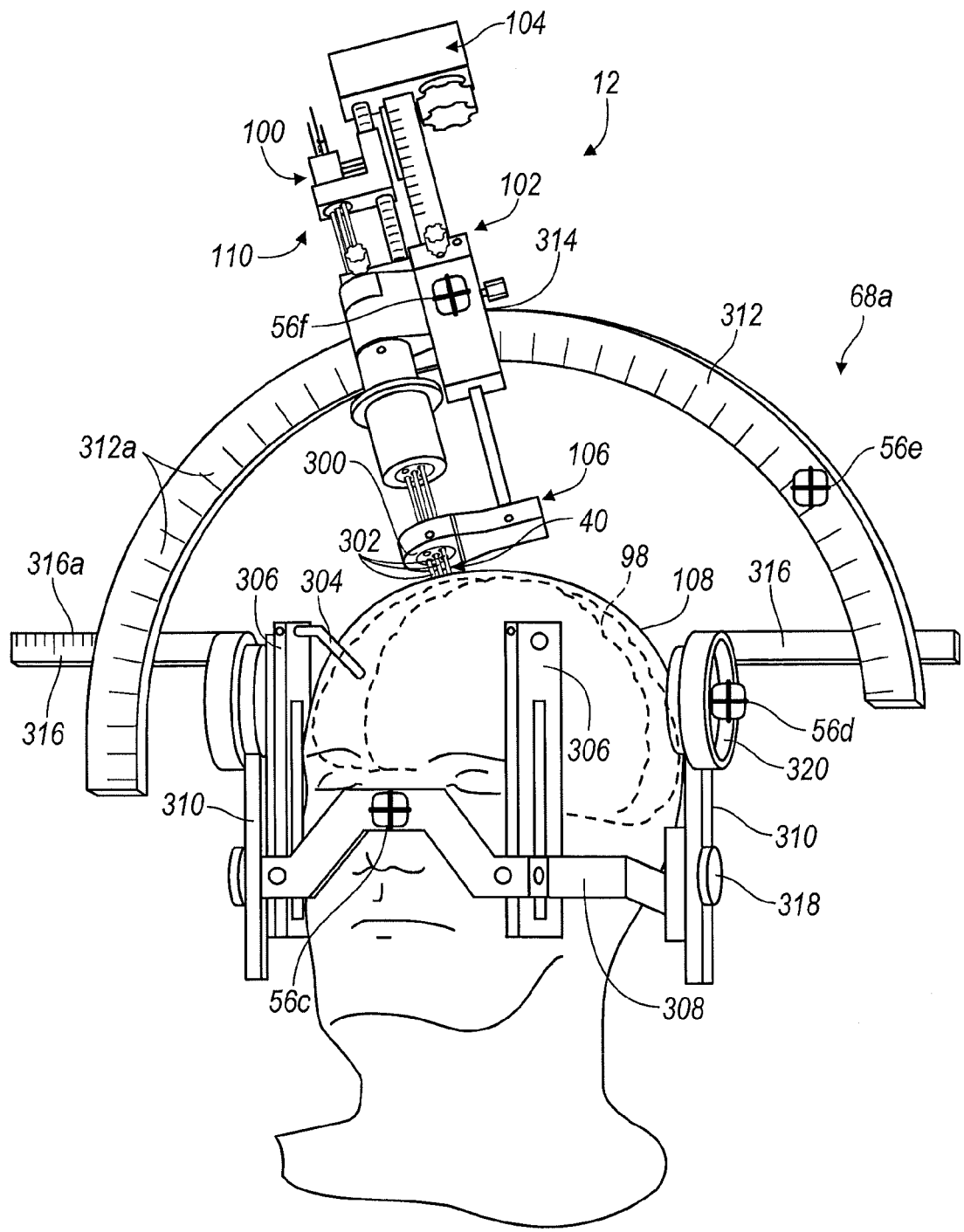
FIG. 2 is a detailed perspective view of the exemplary drive system of FIG. 1 in use with a first exemplary head frame according to various embodiments.
Figure 3:
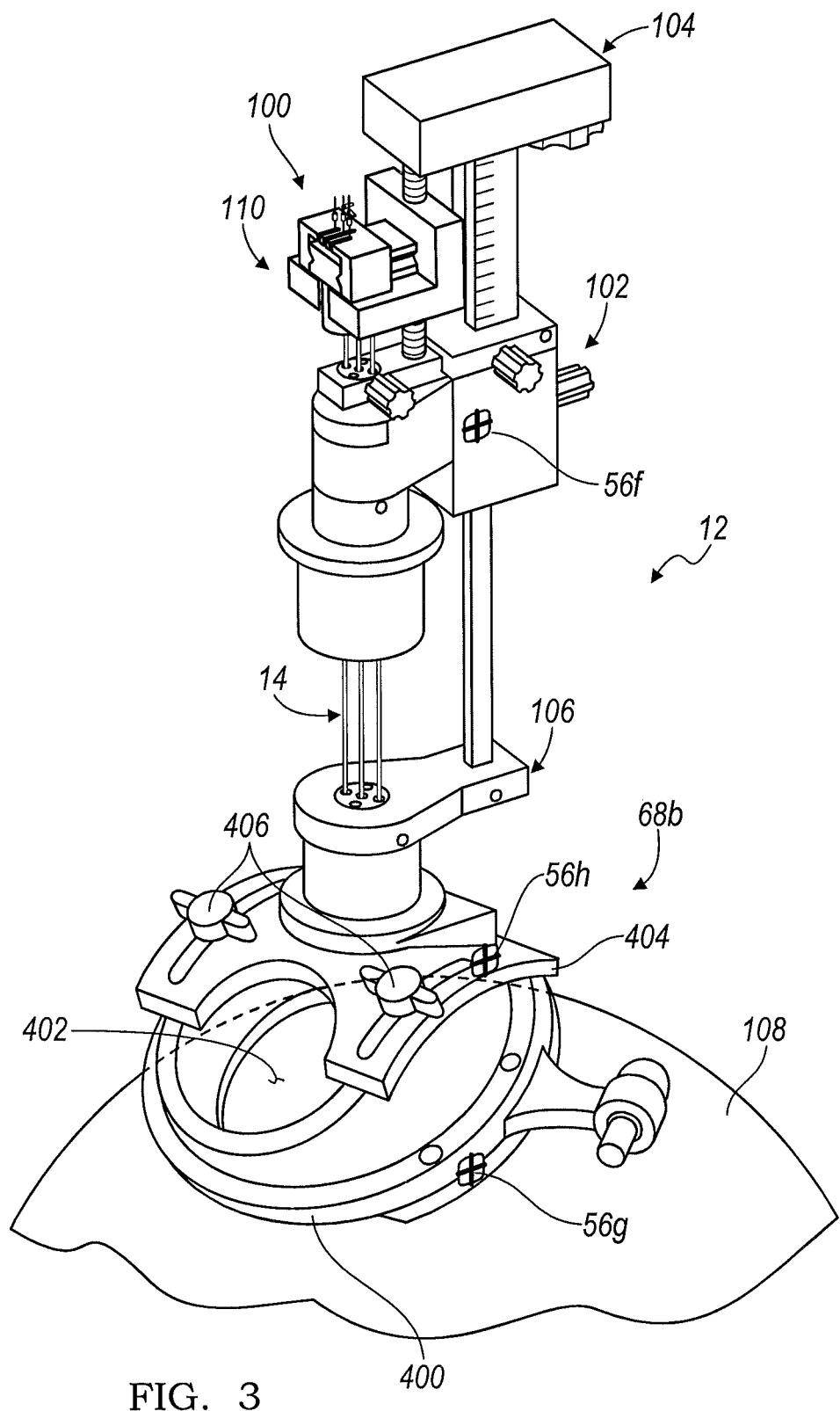
FIG. 3 is a detailed perspective view of the exemplary drive system of FIG. 1 in use with a second exemplary head frame according to various embodiments.

With continued reference to FIG. 1 and with additional reference to FIG. 2 and 3, the guide or drive system 12 for use with an exemplary head frame 68, such as a stereotactic head frame 68a (FIG. 2) or a small scale sterotactic head frame 68b (FIG. 3) is illustrated. The drive system 12 can be used to drive various instruments, such as one or more instruments 14, such as electrodes, into an anatomy, such as a brain 98. As will be discussed in greater detail herein, a procedure on the brain 98 can include a recorder for detecting electrical activity in the brain 98 with a microelectrode (ME) or macroelectrode. Once a recording of the brain 98 has occurred, a stimulator probe, such as a deep brain stimulator probe or a macroelectrode can be delivered to an area identified with the ME or macroelectrode. Generally, the ME or macroelectrode, after identifying an area of interest in the brain 98, can be removed and the stimulator probe can be driven and guided along a similar or identical trajectory or axis relative to the removed ME or macroelectrode. The stimulator probe can be provided to electrically stimulate the selected region of the anatomy, either short term or long term.

With reference to FIG. 2, the drive system 12 can include any appropriate drive system. The drive system 12 can include a driven or control portion 100, a connector rod or support portion 102, a drive portion 104 and a guide system 106. The control portion 100, support portion 102 and a portion of the drive portion 104 of the drive system 12 can comprise the microTargeting Drive® system produced by Fred Haer Corp., FHC Inc. of 9 Main Street, Bowdoinham Me. 04008, USA. The drive system 12 can be interconnected with various guide or support portions, such as the stereotactic head frame 68a (FIG. 2), the small-scale head frame 68b (FIG. 3), robotic devices, or guide devices, to drive various instruments into selected portions of the anatomy. For example, the stereotactic head frame 68a can comprise any suitable stereotactic head frame known in the art, such as the Leksell Stereotactic System® provided by Elekta AB, and the small-scale head frame 68b can be any appropriate mechanism, such as the NEXFRAME™ sold by Medtronic Image Guided Neurologics of Minnesota, USA. The drive system 12 can be interconnected with the head frames 68 to position the drive system 12 at any appropriate location to drive various instruments 14 into a cranium 108. Any appropriate instruments 14 can be advanced by the drive system 12 into the anatomy, including those examples discussed herein, such as electrodes. For example, the drive system 12 can drive ME, DBS probes, macroelectrode stimulators, or other appropriate instruments. In addition, although the drive system 12 will be discussed and illustrated herein as advancing a plurality of instruments 14 into the anatomy, it should be understood that the drive system 12 can be used to advance any desirable number of instruments 14 into the anatomy, from one to numbers greater than five.

With continued reference to FIGS. 2 and 3, the drive system 12 can be used to advance, drive or move selected instruments 14 with the control portion 100 based on torque received from the drive portion 104. The drive portion 104 can be electrically or manually powered to drive an instrument holding system or section 110. The instrument holding section 110 can secure the plurality of instruments 14 to the drive system 12 so that the drive system 12 can be used to advance the instruments 14 into the anatomy. The instrument holding section 110 can optionally include one or more tracking devices 56, if desired. With additional reference to FIG. 4, the instrument holding section 110, according to various embodiments, can include an array holder 112 and a fixation plate 114.

The array holder 112 can receive the instruments 14 for insertion into the anatomy. The array holder 112 can be coupled to a support 104a of the drive portion 104, and thus, can be in communication with the drive system to receive a driving force to guide the instruments 14 into the anatomy. The array holder 112 can include a fixation block 116 and a guide member 118. Each of the fixation block 116 and the guide member 118 can define at least one or a plurality of bores 120 for receipt of the instrument(s) 14 therethrough. It should be noted that although the array holder 112 is illustrated as two distinct parts in FIG. 4, the array holder 112 can be integrally formed, machined or molded from a suitable biocompatible material. Generally, the array holder 112 can be a single-use item that is replaced after each surgery, but the array holder 112 could also be configured as a multiple-use device.

Figure 4:
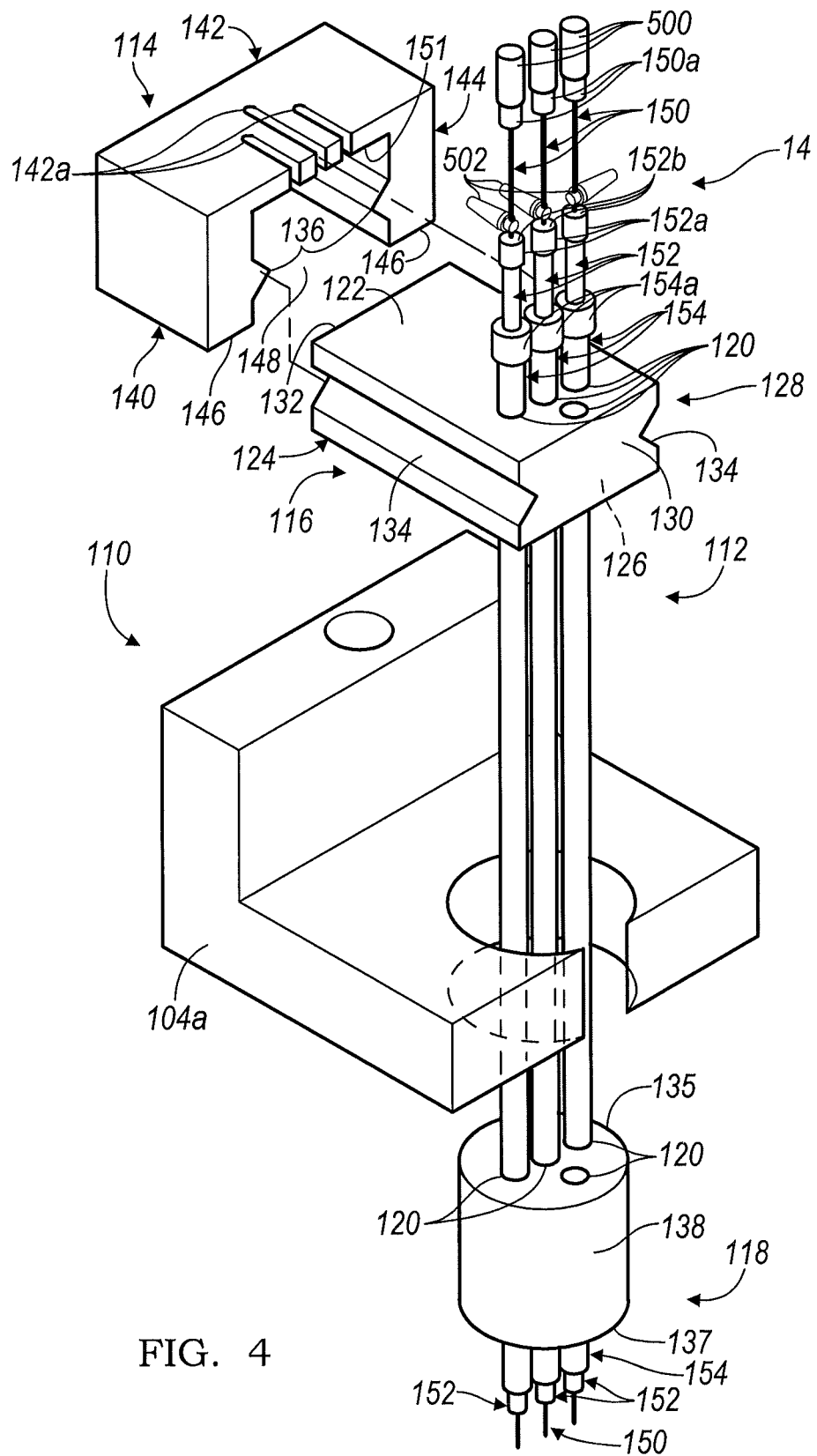
FIG. 4 is an exploded view of an exemplary instrument holding section for use with the exemplary drive system of FIG. 1, which provides cannula fixation for an array insertion tube set according to one of various embodiments.
Figure 5:
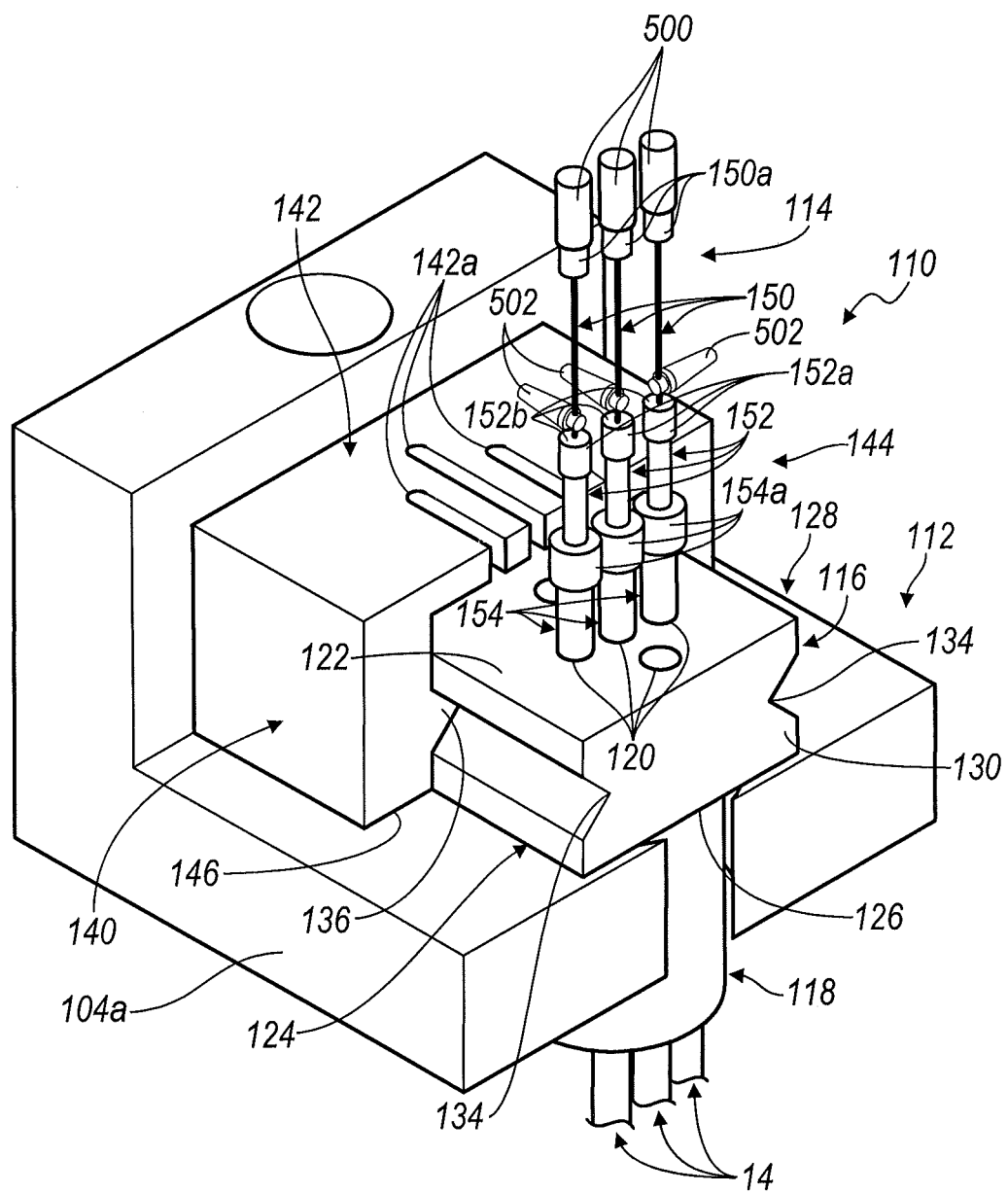
FIG. 5 is an detailed perspective view of the exemplary instrument holding section of FIG. 4 in a first position.
Figure 6:
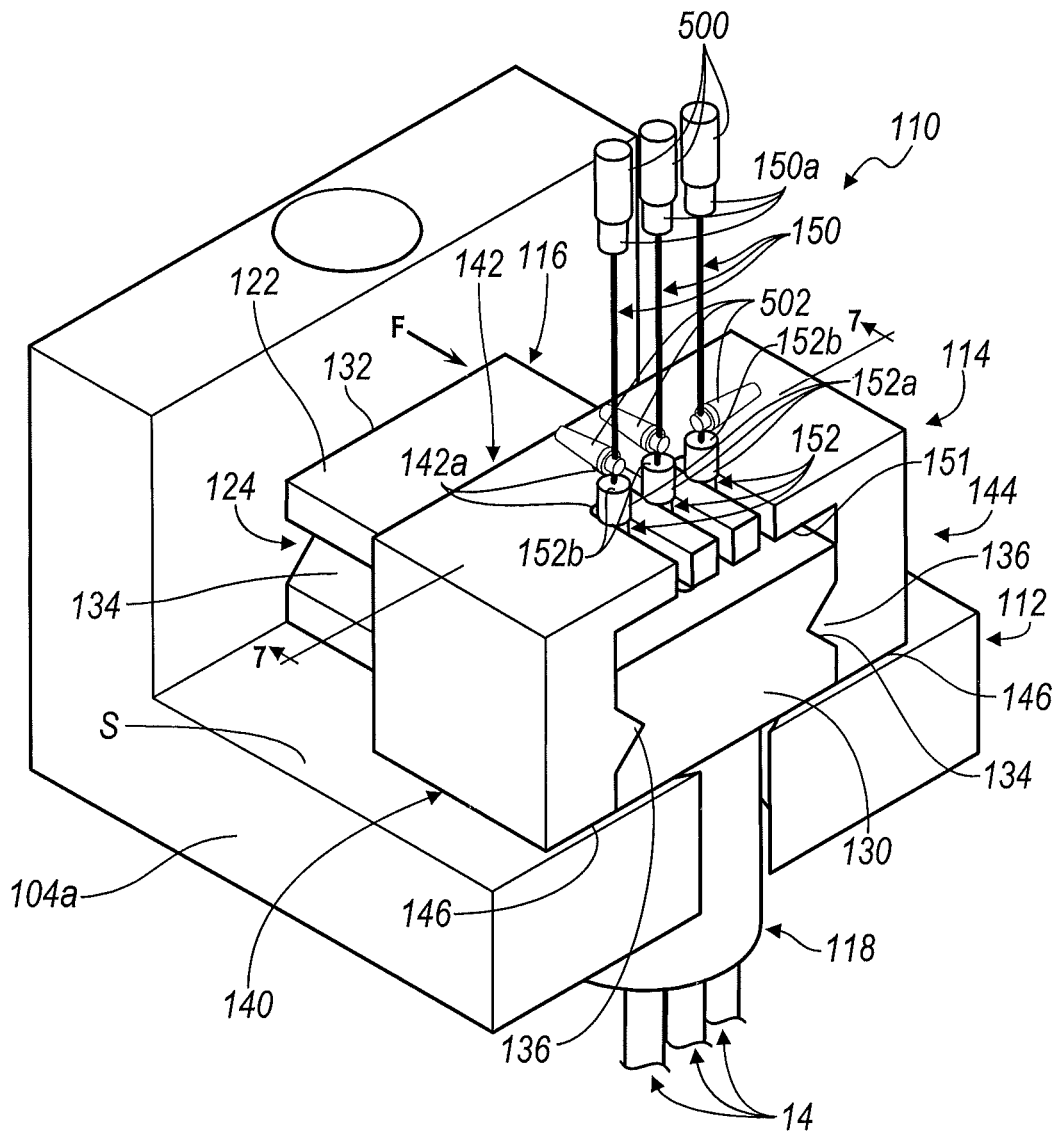
FIG. 6 is an detailed perspective view of the exemplary instrument holding section of FIG. 4 in a second position.

With reference to FIGS. 4-7, the fixation block 116 can include a first side 122, a second side 124, a third side 126, a fourth side 128, a first end 130 and a second end 132. The first side 122 can be generally parallel and opposite to the third side 126, and the second side 124 can be generally parallel and opposite to the fourth side 128. The bores 120 can extend through the first side 122 of the fixation block 116 to the third side 126. The second side 124 and fourth side 128 can generally be configured to slideably engage the fixation plate 114, as will be discussed herein. Briefly, however, the second side 124 and the fourth side 128 can be configured such that the fixation plate 114 can slide from the second end 132 (FIG. 5) of the fixation block 116 to the first end 130 (FIG. 6). The bores 120 can be positioned adjacent to the first end 130 such that the fixation plate 114 can be moved in and out of contact with the instrument(s) 14 disposed in the bores 120 (FIG. 7), as will be discussed.

In the example of FIGS. 4-7, the second side 124 and the fourth side 128 can include a mating feature or groove 134, which can be shaped to correspond or mate with a corresponding mating feature, such as a notch 136 formed in the fixation plate 114. In this example, the groove 134 can comprise a V-shaped groove, however, it will be understood that the groove 134 can comprise any desired shape, such as U-shaped, and further, that more than one groove 134 can be employed, if desired. The groove 134 can mate with the notch 136 of the fixation plate 114 to enable the fixation plate 114 to move or slide relative to the fixation block 116. The third side 126 of the fixation block 116 can be coupled to the guide member 118, as shown in FIG. 5.

With reference to FIGS. 4-7, the guide member 118 can support the instruments 14 as the instruments 14 are advanced into the anatomy by the drive portion 104. The guide member 118 is illustrated as being cylindrical, however, it will be understood that the guide member 118 can comprise any desired shape, such as cubic, etc. The guide member 118 can include a first end 135, a second end 137 and a side wall 138. The bores 120 can extend through the guide member 118 from the first end 135 to the second end 137. The first end 135 can be coupled to the fixation block 116, and the second end 137 can be opposite the first end 135. The side wall 138 can be configured to be coupled to the support 104a of the drive portion 104 to enable the application of the torque from the drive portion 104 to the array holder 112 to advance the instrument(s) 14 within the array holder 112 into the anatomy. The side wall 138 can be coupled to the support 104a, via any appropriate means, such as press-fit, mechanical fasteners, adhesive, etc.

With continued reference to FIGS. 4-7, the fixation plate 114 can couple, clamp or secure the instrument(s) 14 to the array holder 112. The fixation plate 114 can be slideably coupled to the support 104a of the drive portion 104 to enable the fixation plate 114 to move relative to the array holder 112. The fixation plate 114 can generally be configured as a single-use medical device, however, the fixation plate 114 can be configured for multiple-uses, if desired. In one example, the fixation plate 114 can include a first side 140, a second side 142, a third side 144, a fourth side 146 and can define an aperture 148. The first side 140 can be disposed opposite the third side 144, and each of the first side 140 and the third side 144 can include the notch 136. The second side 142 can include at least one or a plurality of slots 142a, which can enable at least a portion of the instrument(s) 14 within the array holder 112 to pass therethrough, while still maintaining contact with the instrument(s) 14 within the array holder 112.

Figure 7:
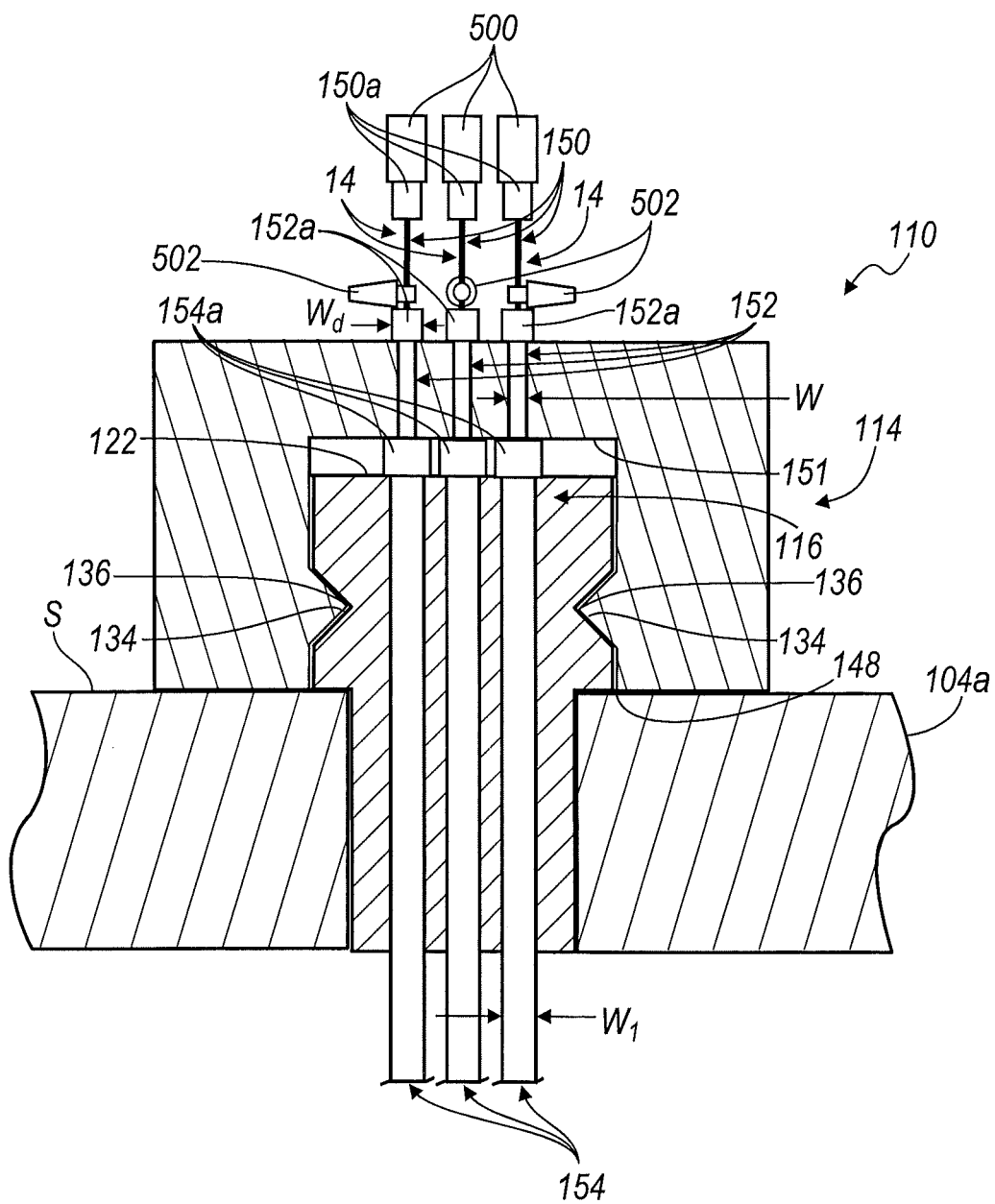
FIG. 7 is a cross-sectional view of the exemplary instrument holding section of FIG. 4, taken along line 7-7 of FIG. 6.

In this regard, the instrument 14 can include an ME 150 and a macroelectrode 152, which can pass through the slots 142a such that an inner surface 151 of the fixation plate 114 can be positioned against a depth stop 154a of an insertion cannula 154 of each of the instruments 14 to ensure that each of the instruments 14 move with the drive portion 104, as shown in FIG. 7. Generally, the macroelectrode 152 can be disposed within the insertion cannula 154, as will be discussed in greater detail herein. The macroelectrode 152 can include a bore for receipt of one of the MEs 150. The macroelectrode 152 and ME 150 can be inserted into the insertion cannula 154 such that the drive portion 104 can be operable to advance each of the macroelectrode 152 and ME 150 by advancing the insertion cannula 154. In this regard, each ME 150 can include a depth stop 150a, and each macroelectrode 152 can include a depth stop 152a. The ME 150 can be inserted into the macroelectrode 152 until the depth stop 150a contacts the macroelectrode 152, and thereby prevents the further advancement of the ME 150. Similarly, the macroelectrode 152 can be inserted into the insertion cannula 154 until the depth stop 152a contacts the insertion cannula 154, and thereby prevents the further advancement of the macroelectrode 152. It will be understood, however, that the ME 150 can be inserted into the macroelectrode 152 to any desired depth up to the depth stop 150a, and the macroelectrode 152 can be inserted into the insertion cannula 154 at any desired depth up to the depth stop 152a.

The slots 142a can have a width W, which can be less than a width W1 of the insertion cannula 154, but greater than a width $W_d$ of the depth stop 152a of the macroelectrode 152. The fourth side 146 of the fixation block 114 can be adjacent to and slideable on a surface S of the support 104a. The aperture 148 can be sized to such that the fixation plate 114 can move or slide over the fixation block 116 of the array holder 112, but can have a tolerance such that a force F can be required to move the fixation plate 114 relative to the fixation block 116.

With reference to FIGS. 4-7, generally, in order to couple, clamp or secure the instrument(s) 14 to the drive portion 104 of the drive system 12, the instrument(s) 14, such as the insertion cannula 154, can be inserted through the bores 120 defined in the array holder 112 (FIG. 4). The MEs 150 and the macroelectrodes 152 can then be inserted or pressed into the insertion cannula 154 such that the drive portion 104 can advance the insertion cannulas 154, the macroelectrodes 152 and the MEs 150 by driving the instrument holding section 110. In this regard, the insertion cannula 154 can be positioned within the fixation block 116 such that the fixation plate 114, when positioned, can apply a driving force to each depth stop 154a of the insertion cannulas 154 to advance the instruments 14 into the anatomy. Once the instrument(s) 14 are positioned within the fixation block 116, the force F can be applied to the fixation plate 114 to move or slide the fixation plate 114 from a first position at the second end 132 of the fixation block 116 (FIG. 5) to a second position at the first end 130 of the fixation block 116 (FIG. 6). Typically, as shown in FIG. 7, the instruments 14 can be inserted into the fixation block 116 such that when the fixation plate 114 is in the second position, the macroelectrode 152 extends through the slots 142a, and the inner surface 151 can be adjacent to the depth stop 154a of the insertion cannula 154 associated with each of the instruments 14. The fixation plate 114 can cooperate with the drive portion 104 to apply about an equal force to each of the insertion cannulas 154 to ensure that the insertion cannulas 154 advance substantially simultaneously into the anatomy. In other words, the fixation plate 114 can apply a constant force against each of the insertion cannulas 154 such that as the drive portion 104 advances the instrument holding section 110 toward the anatomy, all of the insertion cannulas 154 are pulled toward the anatomy, via the contact between the depth stop 154a of the insertion cannulas 154 and the fixation plate 114. It will be understood, however, that the fixation plate 114 could be configured so that the inner surface 151 contacts the depth stop 152a of the macroelectrode 152 or the depth stop 150a of the ME 150 to drive the instruments 14 into the anatomy, if desired.

Figure 8:
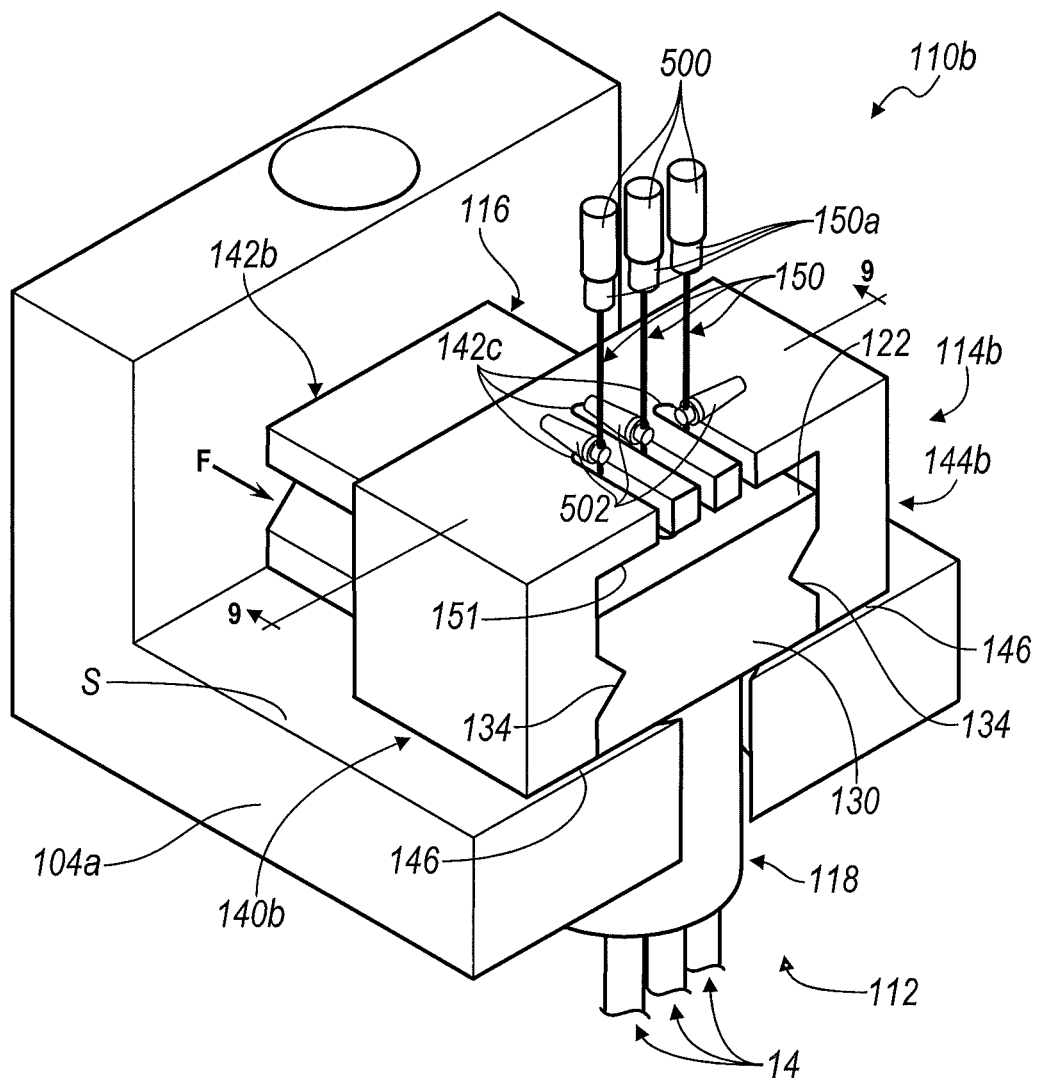
FIG. 8 is a detailed perspective view of an exemplary instrument holding section for use with the exemplary drive system of FIG. 1, which provides cannula fixation for an array insertion tube set according to one of various embodiments.
Figure 9:
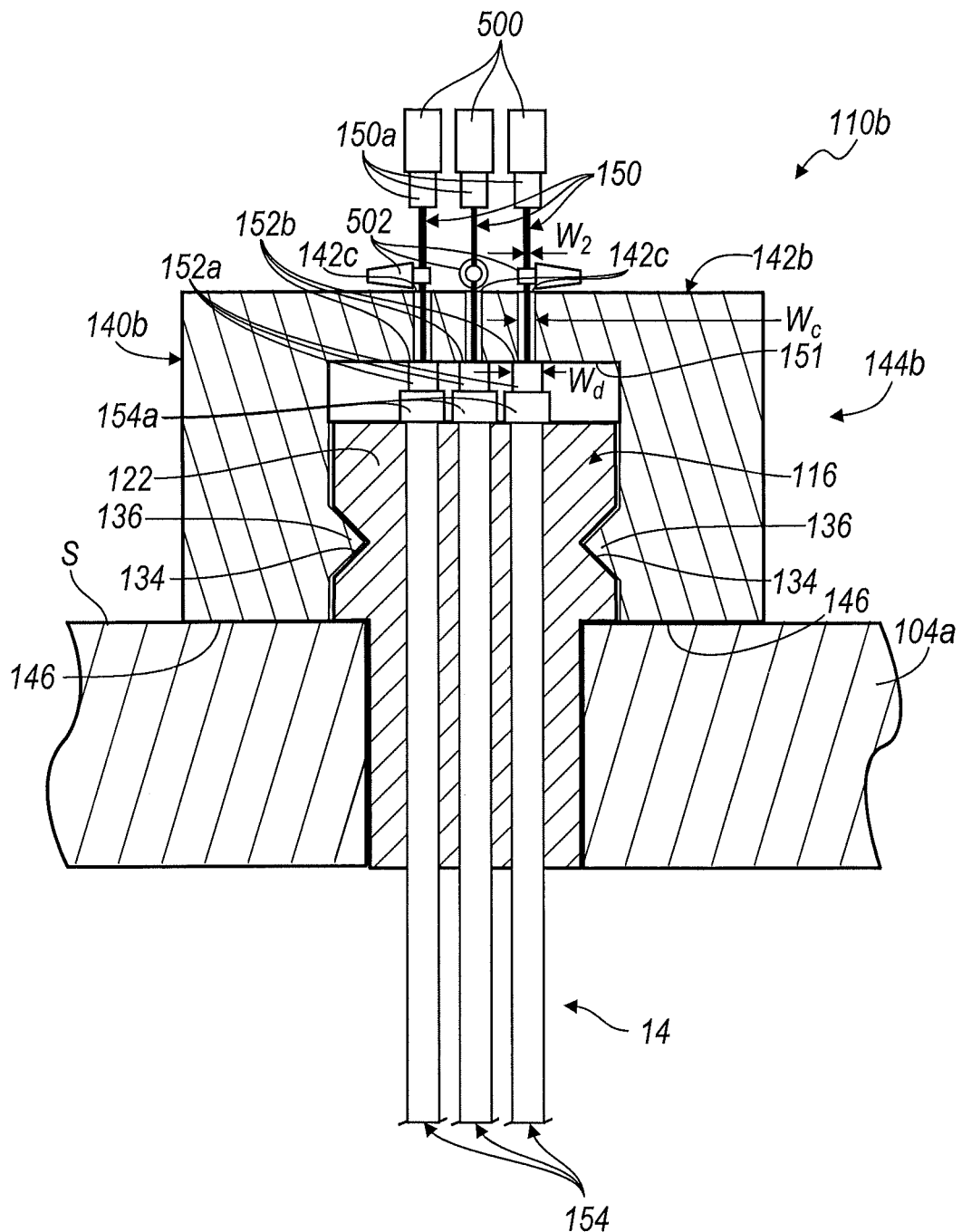
FIG. 9 is a cross-sectional view of the exemplary instrument holding section of FIG. 8, taken along line 9-9 of FIG. 8.

With reference to FIGS. 8-9, in one of various embodiments, an instrument holding section 110b for use with the support 104a of the drive portion 104 is shown. As the instrument holding section 110b can be similar to the instrument holding section 110 described with reference to FIGS. 1-7, only the differences between the instrument holding section 110 and the instrument holding section 110b will be discussed in great detail herein, and the same reference numerals will be used to denote the same or similar components. The instrument holding section 110b can include the array holder 112 and a fixation plate 114b.

The fixation plate 114b can couple, clamp or secure the instrument(s) 14 to the array holder 112. In one example, the fixation plate 114b can include a first side 140b, a second side 142b, a third side 144b, the fourth side 146 and can define the aperture 148. The first side 140b can be disposed opposite the third side 144b, and each of the first side 140b and the third side 144b can include the notch 136. The first side 140b and the third side 144b can be configured to enable the slots 142c of the second side 142b to contact the depth stop 152a of each of the instruments 14 as shown in FIG. 9. In this regard, a portion of the ME 150 of the instrument 14 can pass through the slots 142c such that the inner surface 151 of the fixation plate 114b can be positioned against a top surface 152b of the depth stop 152a of each of the macroelectrodes 152 of the instruments 14 to ensure that each of the instruments 14 move substantially simultaneously with the drive portion 104. Thus, the slots 142c can have a width Wc, which can be less than a width Wd of the depth stop 152a, but greater than a width W2 of the ME 150.

Accordingly, in order to couple, clamp or secure the instruments 14 to the drive portion 104 of the drive system 12, with the instruments 14 inserted through the bores 120 of the array holder 112 so that the depth stop 154a of the insertion cannula 154 is adjacent to the first side 122 of the fixation block 116, and the macroelectrode 152 and the ME 150 inserted within the insertion cannula 154, the force F can be applied to the fixation plate 114. The force F can move or slide the fixation plate 114b from the first position at the second end 132 of the fixation block 116 to the second position at the first end 130 of the fixation block 116 (FIG. 8). Typically, as shown in FIG. 9, the electrodes 14 can be inserted into the fixation block 116 such that when the fixation plate 114b is in the second position, a portion of the ME 150 extends through the slots 142c, and the inner surface 151 can be adjacent to the top surface 152b of the depth stop 152a associated with each of the macroelectrodes 152. As the macroelectrodes 152 are coupled to the insertion cannulas 154, the application of the constant force to the depth stop 152a can serve to advance the MEs 150, the macroelectrodes 152 and the insertion cannulas 154 towards the anatomy. Thus, the fixation plate 114b can cooperate with the drive portion 104 to apply about an equal force to each of the instruments 14, via the depth stop 152a of each of the macroelectrodes 152, to ensure that the instruments 14 advance substantially simultaneously into the anatomy.

Figure 10:
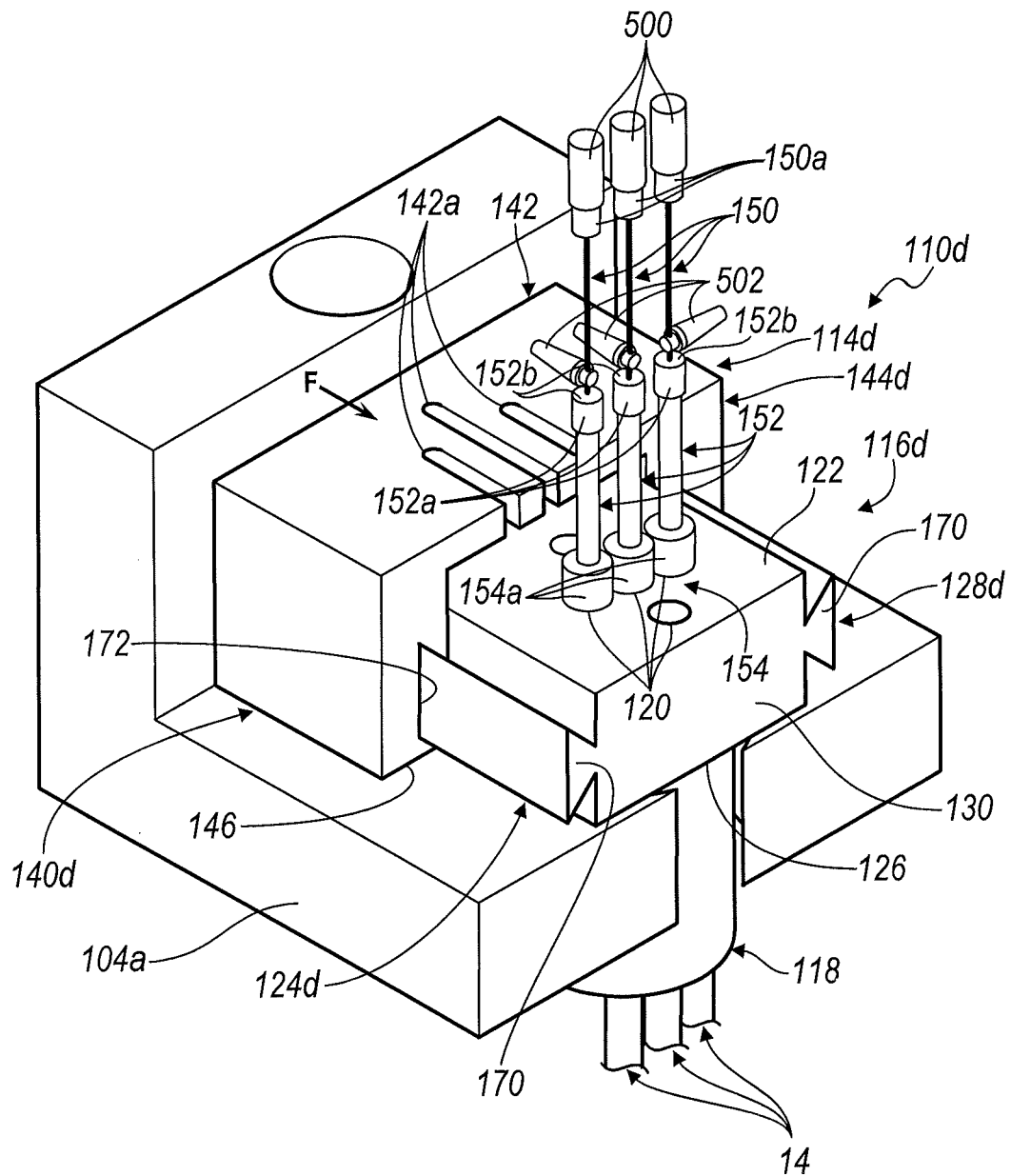
FIG. 10 is an detailed perspective view of an exemplary instrument holding section for use with the exemplary drive system of FIG. 1, which provides cannula fixation for an array insertion tube set according to one of various embodiments.

With reference to FIG. 10, in one example, an instrument holding section 110d for use with the support 104a of the drive portion 104 is shown. As the instrument holding section 110d can be similar to the instrument holding section 110 described with reference to FIGS. 1-7, only the differences between the instrument holding section 110 and the instrument holding section 110d will be discussed in great detail herein, and the same reference numerals will be used to denote the same or similar components. The instrument holding section 110d can include an array holder 112d and a fixation plate 114d.

The array holder 112d can receive the instruments 14, and can be coupled to a support 104a of the drive portion 104. The array holder 112 can include a fixation block 116d and the guide member 118. The fixation block 116d can define the bores 120 for receipt of the instrument(s) 14 therethrough, and can be integrally formed with the guide member 118, if desired. The fixation block 116d can include the first side 122, a second side 124d, the third side 126, a fourth side 128d, the first end 130 and the second end 132. The second side 124d can be generally parallel to the fourth side 128d, and can generally be configured to slideably engage the fixation plate 114d. In the example of FIG. 10, the second side 124d and the fourth side 128d can include a dovetail 170, which can be shaped to correspond or mate with a cut-out 172 formed in the fixation plate 114d. The dovetail 170 can mate with the cut-out 172 of the fixation plate 114d to enable the fixation plate 114d to move or slide relative to the fixation block 116d.

The fixation plate 114d can couple, clamp or secure the instrument(s) 14 to the array holder 112d. In one example, the fixation plate 114d can include a first side 140d, the second side 142, a third side 144d, the fourth side 146, and can define the aperture 148. The first side 140d can be disposed opposite the third side 144d, and each of the first side 140d and the third side 144d can include the cut-out 172.

Accordingly, in order to couple, clamp or secure the instrument(s) 14 to the drive portion 104 of the drive system 12, the instrument(s) 14, such as the insertion cannulas 154, can be inserted through the bores 120 defined in the array holder 112d. Then, the macroelectrodes 152 and the MEs 150 can be inserted into the insertion cannulas 154. The force F can be applied to the fixation plate 114d to move or slide the fixation plate 114d from the first position at the second end 132 of the fixation block 116d (FIG. 10) to the second position at the first end 130 of the fixation block 116d, along the dovetails 170 of the fixation block 116d. Thus, the fixation plate 114d can couple the instruments 14 to the array holder 112d, via the contact between the inner surface 151 of the fixation plate 114d and the depth stop 154a of the insertion cannulas 154, to enable about an equal force to be applied to each of the instruments 14 to advance all of the instruments 14 into the anatomy.

Figure 11:
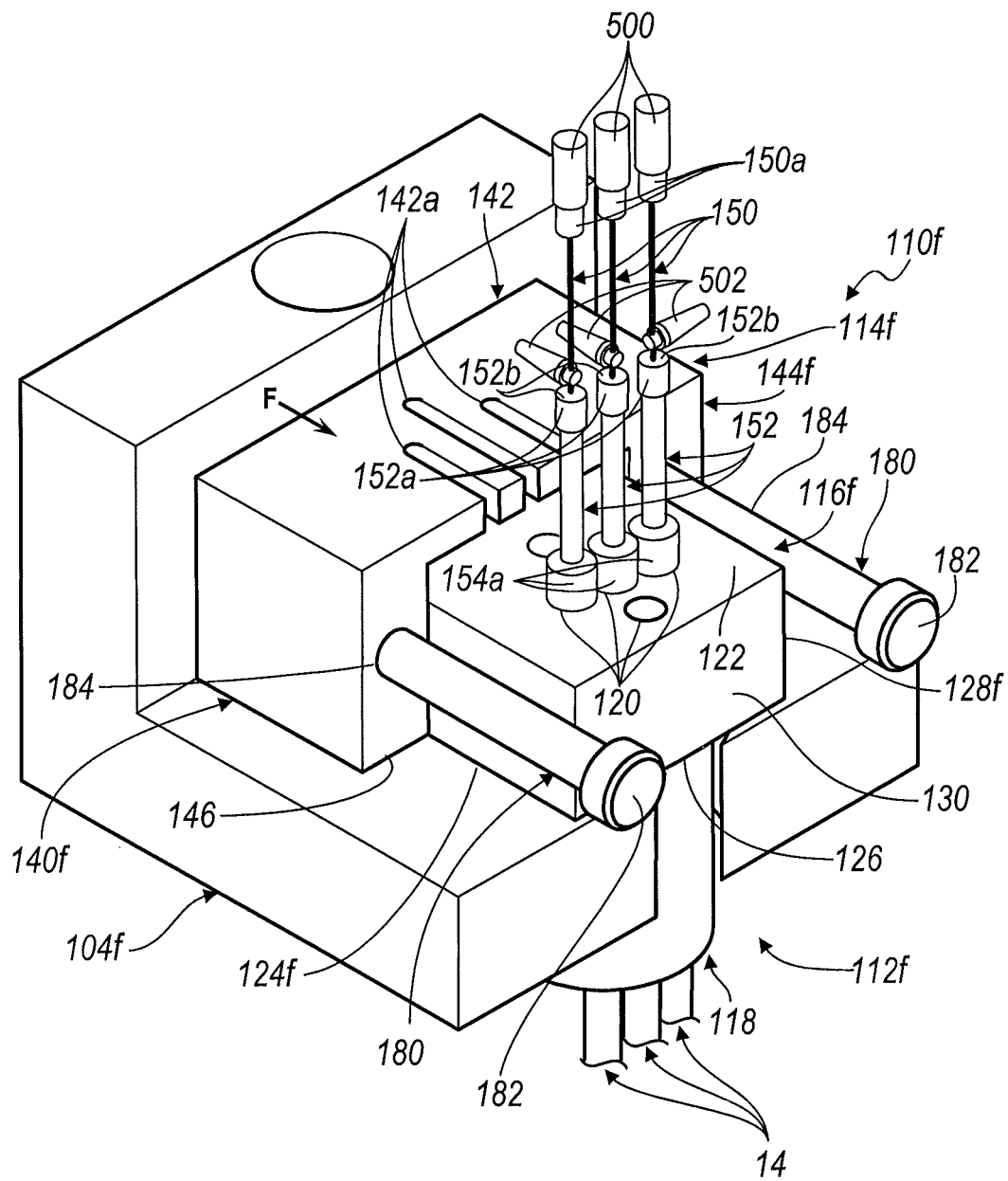
FIG. 11 is a detailed perspective view of an exemplary instrument holding section for use with the exemplary drive system of FIG. 1, which provides cannula fixation for an array insertion tube set according to one of various embodiments.

With reference to FIG. 11, in one example, an instrument holding section 110f for use with a support 104f of the drive portion 104 is shown. As the instrument holding section 110a and support 104f can be similar to the instrument holding section 110 and support 104a described with reference to FIGS. 1-7, only the differences between the instrument holding section 110 and the instrument holding section 110f, and the support 104a and support 104f, will be discussed in great detail herein, and the same reference numerals will be used to denote the same or similar components. The support 104f can include one or more rails 180 to enable the instrument holding section 110f to secure the instrument(s) 14 to the drive portion 104. Each rail 180 can include a flange or end cap 182, which can retain a fixation plate 114f of the instrument holding section 110f to the support 104f. The instrument holding section 110f can include an array holder 112f and the fixation plate 114f.

The array holder 112f can receive the instruments 14, and can be coupled to the support 104f of the drive portion 104. The array holder 112f can include a fixation block 116f and the guide member 118. The fixation block 116f can define the bores 120 for receipt of the instrument(s) 14 therethrough, and can be integrally formed with the guide member 118, if desired. The fixation block 116f can include the first side 122, a second side 124f, the third side 126, a fourth side 128f, the first end 130 and the second end 132. The second side 124f can be generally parallel to the fourth side 128f, and can generally be configured to enable the fixation plate 114f to move or slide relative to the fixation block 116f.

The fixation plate 114f can couple, clamp or secure the instrument(s) 14 to the array holder 112f. In one example, the fixation plate 114f can include a first side 140f, the second side 142, a third side 144f, the fourth side 146, and can define the aperture 148. The first side 140f can be disposed opposite the third side 144f, and each of the first side 140f and the third side 144f can define a throughbore 184.

In order to couple, clamp or secure the instrument(s) 14 to the drive portion 104 of the drive system 12, the instrument(s) 14, such as the insertion cannulas 154, can be inserted through the bores 120 defined in the array holder 112*f*, and the MEs 150 and macroelectrode 152 can be inserted into the insertion cannulas 154 as desired. Then, with the insertion cannulas 154 positioned so that the depth stop 154*a* is adjacent to the first side 122 of the fixation block 116*f*, the force F can be applied to the fixation plate 114*f* to move or slide the fixation plate 114*f*, via the throughbores 184, along the rails 180 of the support 104*f* from the first position at the second end 132 of the fixation block 116*f* to the second position at the first end 130 of the fixation block 116*f*. Thus, the fixation plate 114*f* can couple the instruments 14 to the array holder 112*f* by the contact between the inner surface 151 and the depth stops 154*a* to enable about an equal force to be applied to each of the instruments 14 to advance all of the instruments 14 into the anatomy.

Figure 12:
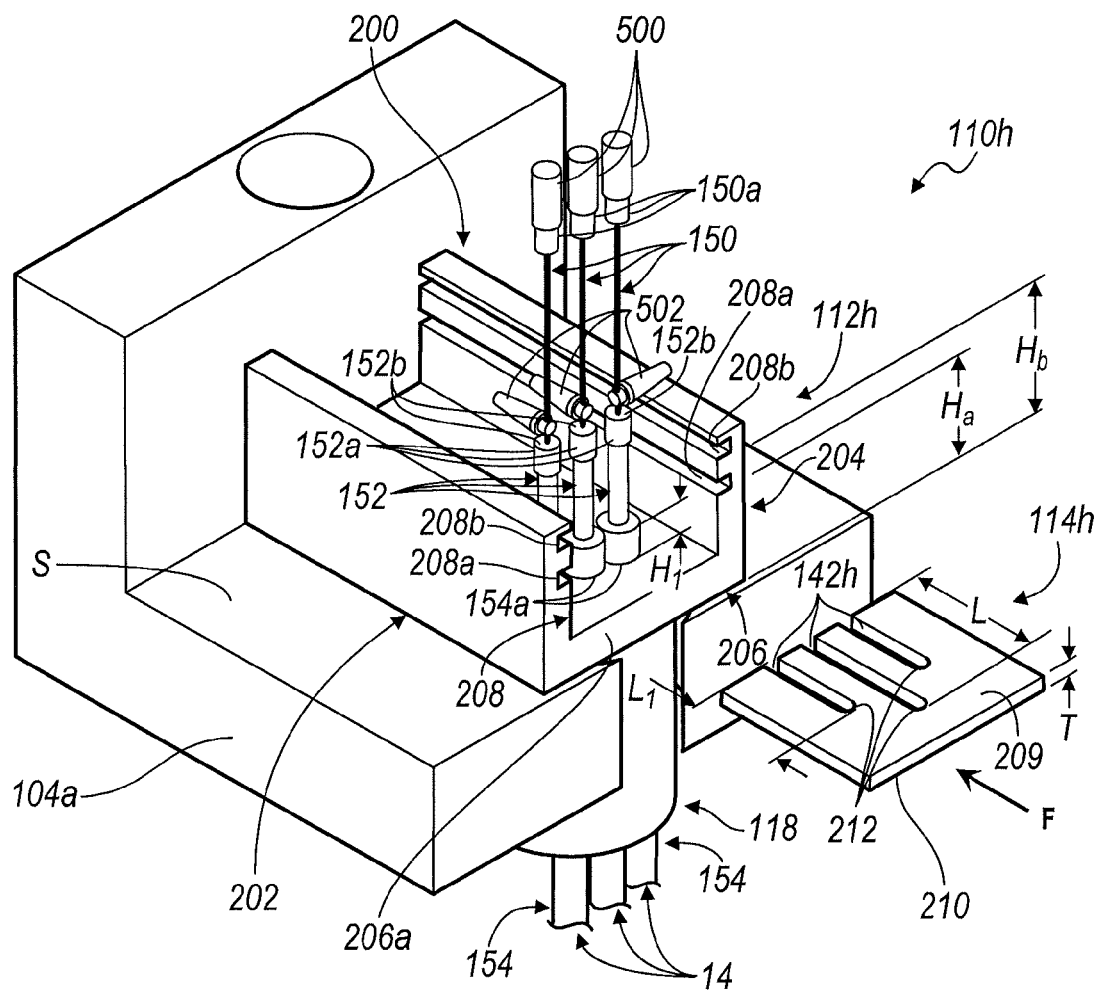
FIG. 12 is a detailed perspective view of an exemplary instrument holding section for use with the exemplary drive system of FIG. 1, which provides cannula fixation for an array insertion tube set according to one of various embodiments, in a first position.
Figure 13:
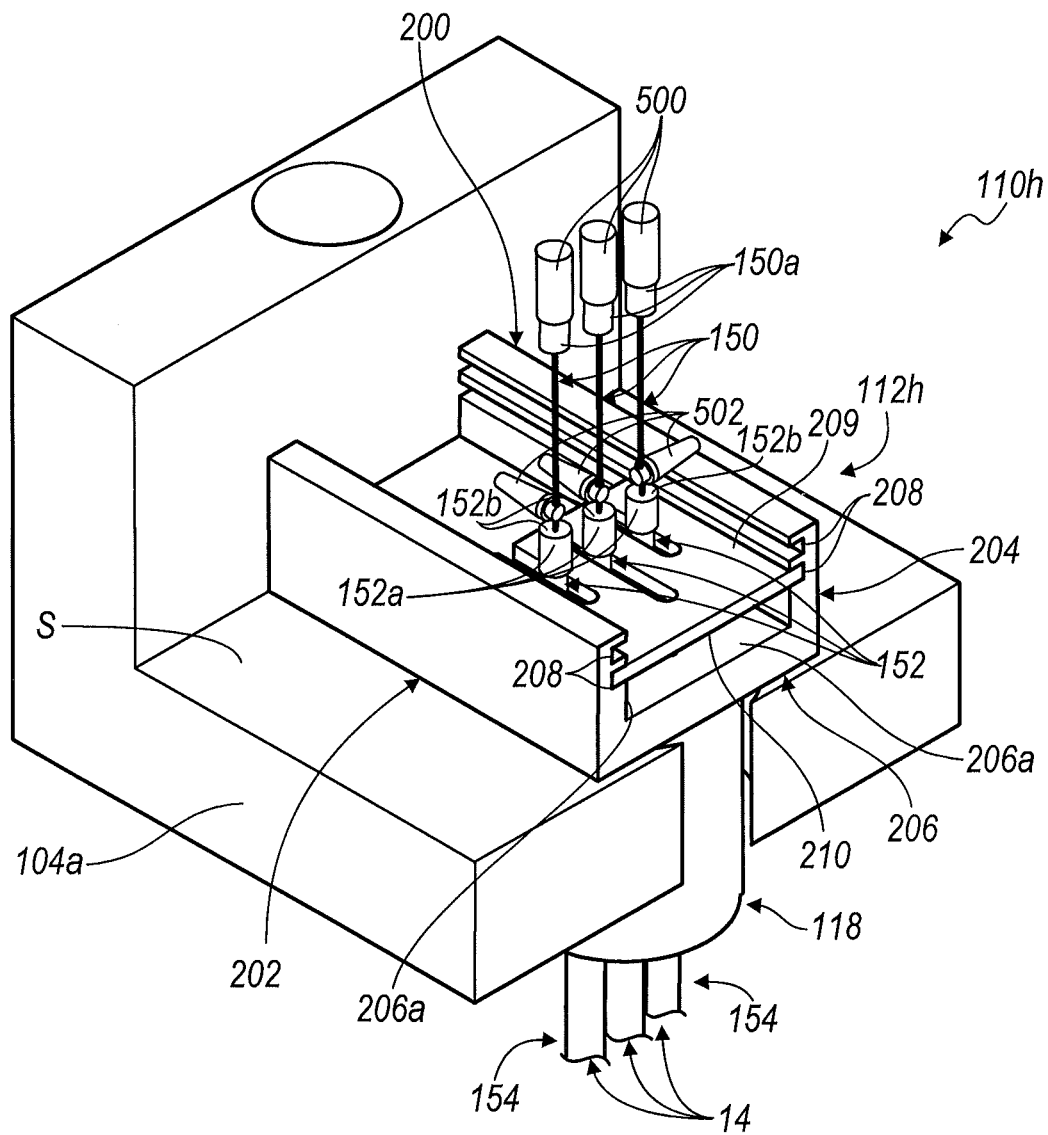
FIG. 13 is a detailed perspective view of the exemplary instrument holding section of FIG. 12, in a second position.

With reference to FIGS. 12-13, according to various embodiments, an instrument holding section 110*h* for use with the support 104*a* of the drive portion 104 is shown. As the instrument holding section 110*h* can be similar to the instrument holding section 110 described with reference to FIGS. 1-7, only the differences between the instrument holding section 110 and the instrument holding section 110*h* will be discussed in great detail herein, and the same reference numerals will be used to denote the same or similar components. The instrument holding section 110*h* can include an array holder 112*h* and a fixation plate 114*h*.

The array holder 112*h* can receive instruments 14, and can be coupled to the support 104*a* of the drive portion 104. The array holder 112 can include a fixation base 200 and the guide member 118. The fixation base 200 can define the plurality of bores 120 for receipt of the instrument(s) 14 therethrough. The fixation base 200 can be generally U-shaped, and can include a first side wall 202, a second side wall 204 and a base 206.

The first side wall 202 can extend generally parallel to the second side wall 204. The first side wall 202 and the second side wall 204 can define at least one or a plurality of slots 208. The slots 208 can slideably receive the fixation plate 114*h*, as will be discussed herein. Generally, first slots 208*a* of the plurality of slots 208 can be formed in the sidewalls 202, 204 at a height $H_a$, which can be about equal to a height $H_1$ of the depth stops 154*a* of the insertion cannulas 154. This can enable the fixation plate 114*h* to contact the depth stops 154*a* of the insertion cannulas 154 to drive the instruments 14 into the anatomy. Second slots 208*b* can be formed in the sidewalls 208, at a height about equal to a height of the depth stop 152*a* and the depth stop 154*a* when the depth stops 152*a*, 154*a* are adjacent to each other (as shown in FIG. 9). Thus, the second slot 208*b* can enable the fixation plate 114*h* to contact the depth stops 152*a* of the macroelectrodes 152 to drive the instruments 14 into the anatomy. The base 206 can be coupled to the guide member 118, and can be disposed adjacent to the support 104*a*. The bores 120 can be defined in the base 206, and can generally be formed adjacent to a first end 206*a* of the base 206.

The fixation plate 114*h* can couple, clamp or secure the instrument(s) 14 to the array holder 112*h*. The fixation plate 114*h* can include a first surface 209, a second surface 210, and can define one or more slots 142*h*. The slots 142*h* can have a length L and $L_1$ which can be sized to act as a stop 212 for the advancement of the fixation plate 114*h* relative to the fixation base 200. The fixation plate 114*h* can have a thickness T, which can be about equal to a width of the slots 208, to enable the fixation plate 114*h* to be slideably received within the slots 208 of the fixation base 200 upon the application of the force F. The second surface 210 can be in contact with the depth stop 154*a* of the insertion cannulas 154 or the depth stop 152*a* of the macroelectrode 152 when the fixation plate 114*h* is coupled to the fixation base 200 (FIG. 13).

In order to couple, clamp or secure the instrument(s) 14 to the drive portion 104 of the drive system 12, the instruments 14 can be inserted through the bores 120 defined in the base 206 of the array holder 112*h*. Then, the fixation plate 114*h* can be aligned with an appropriate slot 208*a*, 208*b* in the fixation base 200, and the force F can be applied to the fixation plate 114*h* to move or slide the fixation plate 114*h* from a first position at the first end 206*a* of the base 206 (FIG. 12) to a second position in which the stop 212 of the slots 142*h* is adjacent to the instrument(s) 14 (FIG. 13), thereby preventing the further advancement of the fixation plate 114*h*. Thus, the fixation plate 114*h* can cooperate with slots 208 of the array holder 112*h* to enable the drive portion 104 to apply about an equal force to each of the instruments 14 in the array holder 112*h* to advance the instruments 14 into the anatomy.

Figure 14:
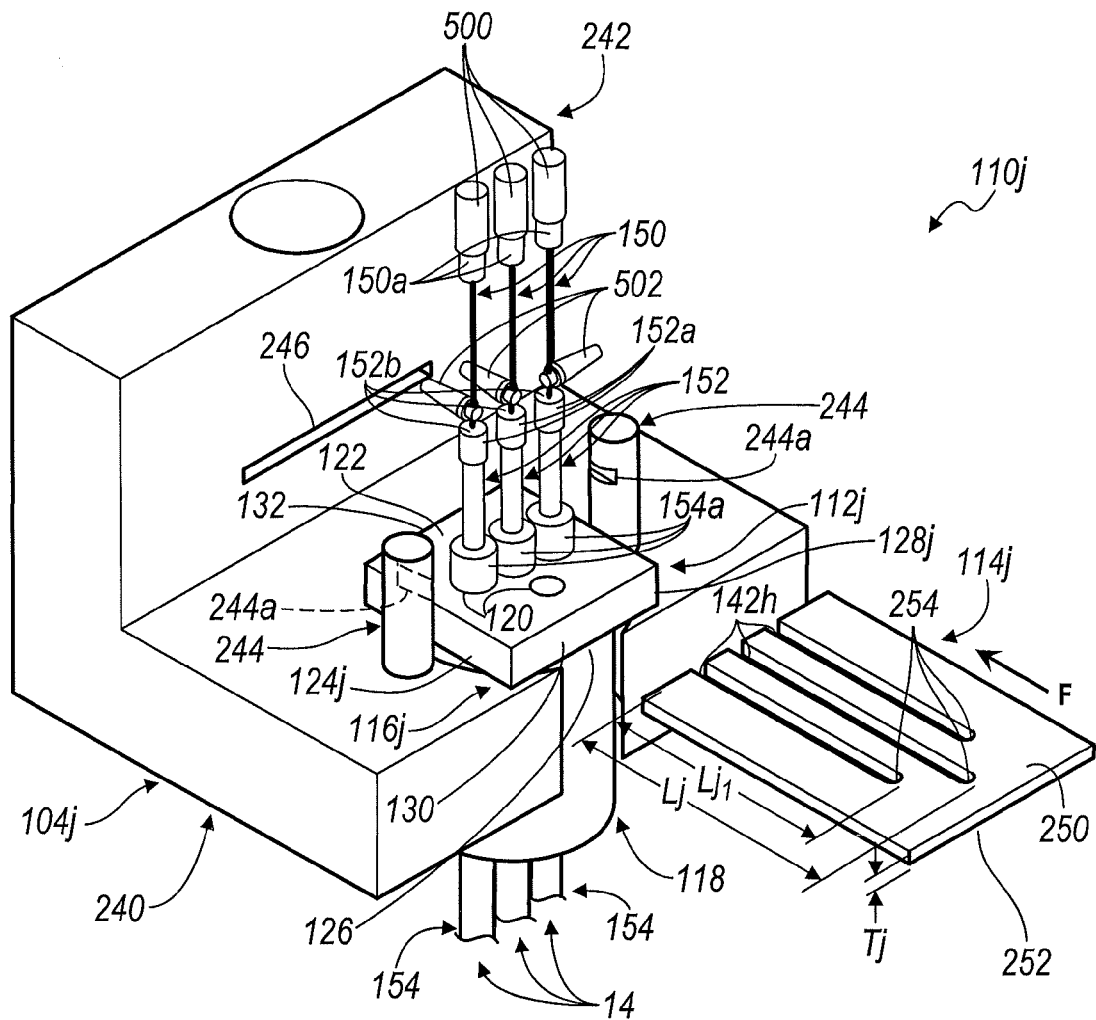
FIG. 14 is a detailed perspective view of an exemplary instrument holding section for use with the exemplary drive system of FIG. 1, which provides cannula fixation for an array insertion tube set according to one of various embodiments, in a first position.
Figure 15:
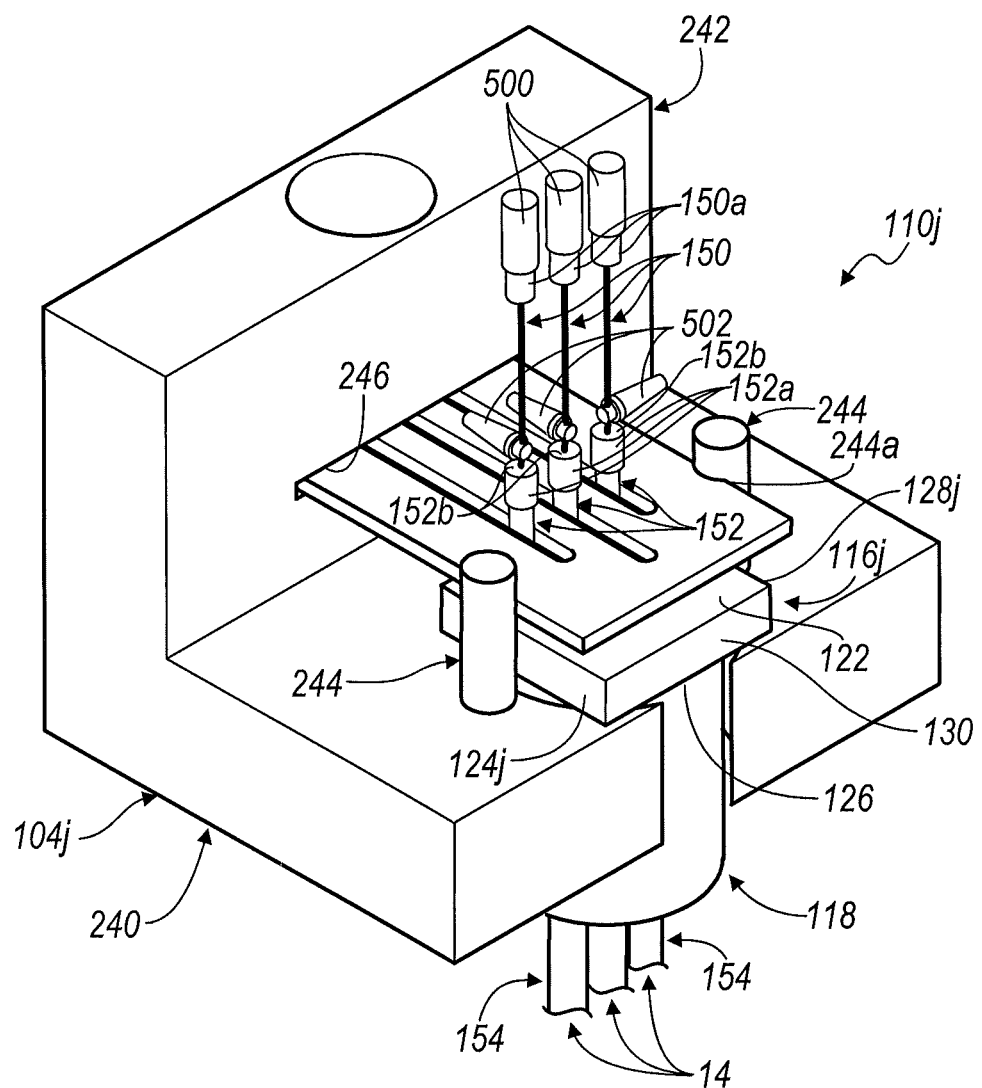
FIG. 15 is a detailed perspective view of the exemplary instrument holding section of FIG. 14, in a second position.

With reference to FIGS. 14-15, in one example, an instrument holding section 110*j* for use with a support 104*j* of the drive portion 104 is shown. As the instrument holding section 110*j* and support 104*j* can be similar to the instrument holding section 110 and support 104*a* described with reference to FIGS. 1-7, only the differences between the instrument holding section 110 and the instrument holding section 110*j*, and the support 104*a* and support 104*j*, will be discussed in great detail herein, and the same reference numerals will be used to denote the same or similar components.

The support 104*j* can include a base 240 and a flange 242. The base 240 can include one or more posts 244. The posts 244 can include slots 244*a*, which can be sized to receive a fixation plate 114*j* associated with the instrument holding section 110*f* therein. The slots 244*a* can cooperate with the fixation plate 114*j* to secure the instrument(s) 14 to the drive portion 104. The flange 242 can extend from the base 240 and can include a slot 246. The slot 246 can receive the fixation plate 114*j* to further couple or secure the fixation plate 114*j* to the support 104*j*.

The instrument holding section 110*j* can include an array holder 112*j* and the fixation plate 114*j*. The array holder 112*j* can receive the instruments 14, and can be coupled to the support 104*j* of the drive portion 104. The array holder 112*j* can include a fixation block 116*j* and the guide member 118. The fixation block 116*j* can define the bores 120 for receipt of the instrument(s) 14 therethrough, and can be integrally formed with the guide member 118, if desired. The fixation block 116*j* can include the first side 122, a second side 124*j*, the third side 126, a fourth side 128*j*, the first end 130 and the second end 132. The second side 124*j* can be generally parallel to the fourth side 128*j*, and can generally be configured to enable the fixation plate 114*j* to move or slide relative to the fixation block 116*j*.

The fixation plate 114*j* can couple, clamp or secure the instrument(s) 14 to the array holder 112*j*. In one example, the fixation plate 114*j* can include a first surface 250, a second surface 252, and can define one or more slots 142*j*. The slots 142*j* can have a length Lj and $Lj_1$, which can be sized to act as a stop 254 for the advancement of the fixation plate 114*j* relative to the fixation block 116*j*. The fixation plate 114*j* can have a thickness Tj, which can be about equal to a width of the slots 244*a* of the posts 244, to enable the fixation plate 114*j* to be slideably received within the slots 244*a* of the support 104*j* upon the application of the force F. The second surface 252 can be in contact with the depth stop 154*a* of the insertion cannulas 154 when the fixation plate 114j is inserted into the slots 244a, and the slot 246 of the flange 242 (FIG. 15).

In order to couple, clamp or secure the instruments 14 to the drive system 12, the insertion cannulas 154 can be inserted through the bores 120 defined in the array holder 112j such that the depth stop 154a can be adjacent to the first surface 122. Then, the macroelectrodes 152 and the MEs 150 can be inserted into the insertion cannulas 154. The fixation plate 114j can be positioned between the posts 244 of the support 104j. The force F can be applied to the fixation plate 114j to move or slide the fixation plate 114j into the slots 244a of the posts 244 and the slot 246 of the flange 242. The fixation plate 114j can be fully coupled to the support 104j when the stop 254 is adjacent to a portion of the macroelectrode 152. Thus, the fixation plate 114j can couple or secure each of the instruments 14 to the array holder 112j to enable about an equal force to be applied to each of the insertion cannulas 154 to substantially simultaneously advance all of the insertion cannulas 154, and thus, the macroelectrodes 152 and the MEs 150, into the anatomy.

With reference back to FIGS. 2 and 3, the drive system 12 in various embodiments can also include the support portion 102. The support portion 102 can hold each of the portions of the drive system 12 during operation. The guide system 106 can cooperate with the drive portion 104 of the drive system 12 to drive the selected instrument(s) 14 into the appropriate portion of the anatomy, such as the cranium 108. One skilled in the art will understand that various gear trains and tracks can be used to transfer a force from the drive portion 104 to the instrument holding section 110.

As the guide system 106 can comprise the guide system as disclosed in commonly owned U.S. patent application Ser. No. 11/733,362, filed Apr. 10, 2007, entitled "System For Guiding Instruments Having Different Sizes," hereby incorporated by reference in its entirety, the guide system 106 will not be described in great detail herein. Briefly, however, the guide system 106 can include an instrument guiding system or portion 300 that can define one or more guide bores 302. The guide bores 302 can be formed in the guide system 106 to guide a selected instrument 14 having a selected dimension. For example, the guide bore 302 can include a diameter that allows for appropriate guiding of a relatively large instrument, such as an electrode, DBS probe, lead, etc. into the anatomy.

The drive system 12 can be interconnected or associated with the stereotactic head frame 68a as illustrated in FIG. 2. As the stereotactic head frame 68a can be any suitable stereotactic head frame known in the art, the stereotactic head frame 68a will not be discussed in great detail herein. Briefly, however, the stereotactic head frame 68a can include various components that are interconnected with the cranium 108. For example, the stereotactic head frame 68a can include fixation pins 304, positioning arms 306, a positioning ring 308, placement arms 310, an arcuate placement track or track 312 and a slide 314.

The fixation pins 304 can extend from connector or positioning arms 306, and can be interconnected to the cranium 108. The positioning arms 306 can be interconnected with the positioning ring 308 at a second end. The positioning ring 308 can include areas to interconnect a plurality of the positioning arms 306 therewith. The placement arms 310 can extend from the positioning ring 308. The placement arms 310 can be interconnected with the track 312, via connecting arms 316. The connecting arms 316 can be moved relative to the positioning ring 308, via a first connection mechanism 318. The connecting arms 316 can be positioned relative to the track 312, via a second connection system 320. The track 312 can also be moveably connected to the connecting arms 316 in any appropriate manner. Therefore, the positioning ring 308 can be fixed to the cranium 108 and the track 312 can be positioned relative to the cranium 108 using the plurality of connection systems 318, 320 and any other appropriate connection mechanism.

The slide 314 can be moved along the track 312 to achieve a selected placement of the slide 314. As illustrated, the track 312 can include calibrated marks 312a for determining a position of the slide 314 relative to the track 312. The connecting arms 316 can also include calibrated marking 316a. The drive system 12 can be interconnected with the slide 314 so that it can be moved relative to the cranium 108 of the patient 16. As one skilled in the art will understand, the slide 314 can be positioned relative to the cranium 108 in a substantially planned manner or selected manner so that the instruments 40 can be driven into the cranium 108 along a selected path. The selected path can ensure the positioning of the instruments 14 in a selected position within the cranium 108. As one skilled in the art will further understand, the path or trajectory of the instruments 14 can be selected based upon a selected final position of the instruments 14 within the brain 98 of the patient 16.

The stereotactic head frame 68a can be positioned by optionally using the navigation system 10, or various other navigation systems, such as that discussed further in U.S. patent application Ser. No. 10/651,267 (now U.S. App. Pub. No. 2005/0049486), entitled "Method and Apparatus for Performing Stereotactic Surgery," incorporated herein by reference. Various tracking devices 56 can be interconnected with the stereotactic head frame 68a such as a first tracking device 56c positioned on the positioning ring 308, a second tracking device 56d positioned on the second connection system 320, a third tracking device 56e positioned on the track 312, and a fourth tracking device 56f positioned on the slide 314 or the drive system 12. The various tracking devices 56c-56f can be used with the tracking system 54 to determine a position of each of the components of the stereotactic head frame 68a, and to determine a position of the slide 314 and/or the drive system 12 relative to the cranium 108. It will be understood, however, that any appropriate stereotactic head frame 68a, either navigated or not, can be used with the drive system 12. In addition, the various tracking devices 56c-56f can be any appropriate type or be used with any appropriate system, such as optical electromagnetic, acoustic, accelerometer, etc.

With reference to FIG. 3, according to various embodiments, the drive system 12 can be interconnected to a smaller or support mechanism or small-scale head frame 68b, as illustrated. The small-scale head frame 68b can include the drive system 12 interconnected therewith. Also, movement of the drive system 12 can be allowed relative to the cranium 108 to ensure an appropriate or selected position of the drive system 12 relative to the cranium 108.

The small-scale head frame 68b can include a base 400 that is fixedly connected to the cranium 108 of the patient 16. The base 400 can define an aperture or opening 402 that allows the instruments 14 to pass through the base 400 into the cranium 108. A moveable base 404 can be interconnected to the base 400 and the drive system 12 can be connected to the moveable base 404. Various set or locking screws 406 can be used to fix the moveable base 404 to a selected position. Further, various markings can be provided on the moveable base 404 or the fixed base 400 to assist in obtaining a selected orientation of the moveable base 404 to the cranium 108.

Further, various tracking devices can be interconnected with the small-scale head frame 68b. For example, a fifth tracking device 56g can be interconnected with the fixed base 400. A sixth tracking device 56h can be interconnected with the moveable base 404. The sixth tracking device 56h can also be used to determine the position of the moveable base 404 relative to the fixed base 400 and the cranium 108. Again, the fourth tracking device 56f can be interconnected with the drive system 12 to determine a position of the drive system 12 relative to the small-scale head frame 68b. The various tracking devices 56f-56h can be used with an optional tracking and navigation system, such as the tracking system 54 and navigation system 10, to determine a position of the various components of the small-scale head frame 68b or the drive system 12 relative the cranium 108 and the brain 98.

The various components of the drive system 12 discussed with reference to FIGS. 1-15 and the stereotactic head frame 68a or the small-scale head frame 68b can be provided to allow for efficient sterilization or sterile use. The stereotactic head frame 68a can be formed of sterilizable materials. The stereotactic head frame 68a, therefore, can be removed after a procedure, cleaned and sterilized for additional procedures. The stereotactic head frame 68a can also be formed of a single use material, either a metal, ceramics, or polymers, but are not limiting to the present teachings. Also, the small-scale head frame 68b can be formed of a rigid polymer to provide for a substantial single use device. Alternatively, the small-scale head frame 68b can be formed of a metal, metal alloy, ceramics, or polymers, but are not limiting to the present teachings, that can also be used for multiple procedures. The drive system 12 can be used with either exemplary head frame 68 to advance each of the instruments 14 substantially simultaneously into the anatomy.

As illustrated in FIGS. 1-15, the drive system 12 can be used to guide one or more exemplary instruments 14, such as one or more electrodes, into the brain 98. The instruments 14 can be used to record activity in the brain 98 and to accurately identify a portion of the brain 98 for stimulation in a first position, and in a second position, a selected one of the instruments 14 can be used to stimulate the selected portion of the brain 98. The instruments 14 can comprise any suitable electrode assembly for insertion into any anatomy, such as the electrodes described in commonly owned U.S. patent application Ser. No. 11/739,791, filed Apr. 25, 2007, entitled "Method And Apparatus For Controlled Insertion and Withdrawal of Electrodes," incorporated by reference herein, and thus, the instruments 14 will not be discussed in great detail herein. Briefly, however, each of the instruments 14 can include the insertion cannula 154, the depth stop 160, the macroelectrode 152, the ME 150, a ground connection 500 and a positive connection 502, as best shown in FIG. 4. The macroelectrode 152 and at least a portion of the ME 150 can pass through the insertion cannula 154 for insertion into the anatomy. Generally, the ME 150 can pass through a bore defined in the macroelectrode 152, and the macroelectrode 152 can pass through a bore defined in the insertion cannula 154. The ground connection 500 can ground the electrode 14, and the positive connection 502 can be coupled to a power source to supply current to the macroelectrode 152, or to record the electrical activity sensed by the ME 150.

The instrument holding section 110 of the present disclosure can enable one or more instruments 14 to be advanced into an anatomy substantially simultaneously. As the fixation plate 114 can apply about an equal force to each of the instruments 14, the fixation plate 114 can ensure that all of the electrodes 14 are advanced to the desired position within the anatomy by the drive system 12, without requiring the operator to make frequent adjustments to the instrument holding section 110. Further, the fixation plate 114 of the instrument holding section 110 can enable an operator to quickly and easily secure each of the instruments 14 to the instrument holding section 110, by moving or sliding the fixation plate 114 relative to the array holder 112. In addition, the instrument holding section 110 can enable the operator to quickly and easily remove one or more instruments 14, if desired, during the surgical procedure. In this regard, the surgeon can simply move or slide the fixation plate 114 from the second position to the first position and then withdraw the desired instrument 14 from the fixation block 116. The fixation plate 114 can then be repositioned over the remainder of the instruments 14 after the desired instrument 14 is removed.

While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description and the appended claims.

In this regard, while the instrument holding section 110 has been described herein as including a fixation plate 114, which can move or slide relative to an array holder 112, those of skill in the art will appreciate that the present disclosure, in its broadest aspects, may be constructed somewhat differently. For example, a cylindrical plate defining multiple apertures could be inserted over the instruments 14 such that the cylindrical plate can be in contact with each of the instruments 14. Then set screws could be employed to retain the cylindrical plate to the portion of the drive portion 104.

What is claimed is:

1. A system comprising:
   a block configured to connect to and receive a driving force from a driver, wherein the block comprises (i) mating surfaces extending in a first direction, and (ii) a first bore extending through the block in a second direction perpendicular to the first direction, and wherein the first bore is configured to guide a first cannula in or out of a patient in the second direction; and
   a guide member connected to the block and having a second bore, wherein the second bore is aligned in the second direction with the first bore of the block; and
   a plate configured to be moved in the first direction relative to the block,
   wherein
      the plate comprises a pair of members and a slot,
      the slot extends in the first direction and is configured to receive a first electrode of the first cannula,
      the pair of members extends from and is perpendicular to the plate,
      the pair of members engages with the mating surfaces of the block such that a gap exists between the block and the plate, wherein the gap is sized such that a first depth stop mounted on the first cannula is received in the gap and on an uppermost surface of the block, and wherein when the plate is slid on the block, the gap exists between the uppermost surface of the block and an opposing inner surface of the plate, and the pair of members is configured to be slid on the mating surfaces such that (i) the first cannula is received in the slot of the plate, (ii) the first depth stop is received in the gap, and (iii) the first cannula is driven by the plate into the patient as a result of the driving force exerted on the block.

2. The system of claim 1, wherein the cannula defines a bore for receipt of the first electrode and a microelectrode, wherein:

the first electrode is a macroelectrode; and
the macroelectrode defines a bore for receipt of the microelectrode.

3. The system of claim 1, wherein:

the block and the guide member define a plurality of bores for guiding a plurality of cannulas in or out of the patient;
the plurality of bores comprise the first bore and the second bore; and
the plurality of cannulas comprise the first cannula.

4. The system of claim 1, wherein the plate or the block is in contact with the first depth stop when the plate is positioned relative to the block such that the first depth stop is in the gap between the plate and the block.

5. The system of claim 1, wherein:

when the plate is positioned relative to the block such that the first depth stop is in the gap between the plate and the block, the plate is in contact with a surface of the first depth stop; and
when in contact with the surface of the first depth stop, the plate and the block prevent movement of the first depth stop relative to the plate and the block.

6. The system of claim 1, wherein:

the mating surfaces of the block are surfaces of two or more structural elements of the block; and
the two or more structural elements include a groove, a notch, a slot, an indentation, or a dovetail.

7. A system comprising:

a first cannula;
a second cannula;
a support member configured to connect to and receive a driving force from a drive system;
a U-shaped member connected to the support member, wherein the U-shaped member comprises a bore, wherein the bore extends in a first direction and is configured to receive the first cannula, wherein the first cannula extends through the bore and comprises a first electrode, and wherein the U-shaped member comprises a plurality of slots extending in a second direction; and
a plate configured to be slid in the plurality of slots to engage with and limit movement of the first electrode of the first cannula relative to the U-shaped member in the first direction, wherein when the plate is slid in the plurality of slots, (i) a gap exists between an inner surface of the U-shaped member and an opposing inner surface of the plate, (ii) the gap is sized to receive a plurality of depth stops, and (iii) the inner surface of the U-shaped member is in contact with the plurality of depth stops, wherein the plurality of depth stops are respectively mounted on the first cannula and the second cannula,
wherein the plate is configured to drive the first electrode into a patient as a result of the driving force exerted on the support member, wherein the first electrode comprises a first connector, and wherein the first connector is at a first voltage potential, and wherein the second cannula is disposed in a second bore of the U-shaped member, wherein the second cannula comprises a second electrode, wherein the second electrode comprises a second connector, and wherein the second connector is at a second voltage potential.

8. The system of claim 7, wherein:

the first electrode comprises a third bore;
the third bore of the first electrode is configured to receive a third electrode; and
the U-shaped member is configured to engage with the plate such that the plate drives the first electrode and the third electrode into the patient as a result of the driving force exerted on the support member.

9. The system of claim 7, wherein:

the plurality of slots comprise a first pair of slots and a second pair of slots;
while the plate is in the first pair of slots, a gap between the plate and the U-shaped member is such that the plate is configured to drive the first electrode and not a third electrode of the first cannula into the patient; and
while the plate is in the second pair of slots, the gap between the plate and the U-shaped member is such that the plate is configured to drive the first electrode and the third electrode into the patient.

10. The system of claim 7, wherein:

the first electrode is a macroelectrode;
the first cannula comprises a microelectrode; and
the macroelectrode defines a bore in which the microelectrode is received.

11. The system of claim 7, wherein the plate is configured to contact and drive the plurality of depth stops in the first direction.

12. The system of claim 1, wherein the the gap is sized such that a plurality of depth stops mounted on a plurality of electrodes of the first cannula fit between the plate and the block;
the plurality of electrodes comprise the first electrode and a second electrode;
the plurality of depth stops comprise the first depth stop and a second depth stop;
the first depth stop is on the first electrode; and
the second depth stop is on the second electrode.

13. The system of claim 1, further comprising the first cannula, wherein the first cannula comprises:

the first electrode; and
a second electrode, wherein the second electrode is disposed in the first electrode.

14. The system of claim 1, further comprising:

the first cannula extending through the first bore, wherein the first electrode comprises a first connector, wherein the first connector is at a first voltage potential, and
wherein the block comprises a third bore; and
a second cannula disposed in the third bore, wherein the second cannula comprises a second electrode, wherein the second electrode comprises a second connector, and wherein the second connector is at a second voltage potential.

15. The system of claim 9, wherein:

when the plate is in the first pair of slots, the gap is sized such that the plurality of depth stops are locked between the plate and the U-shaped member; and
when the plate is in the second pair of slots, the gap is sized such that another depth stop is locked between the plate and the U-shaped member.

16. The system of claim 1, wherein:
the first cannula extends through only a single bore in the block;
the single bore is the first bore; and
the first bore has only a single diameter.

* * * * *